United States Patent
Birkholz et al.

(10) Patent No.: US 11,466,289 B2
(45) Date of Patent: Oct. 11, 2022

(54) NF-KB SIGNALING PATHWAY-MANIPULATED DENDRITIC CELLS

(71) Applicant: Friedrich-Alexander-Universität Erlangen-Nürnberg, Erlangen (DE)

(72) Inventors: Katrin Birkholz, Hohenschäftlarn (DE); Jan Dörrie, Nuremberg (DE); Niels Schaft, Weisendorf (DE); Gerold Schuler, Spardorf (DE); Reinhard Voll, Freiburg (DE); Isabell Pfeiffer, Munich (DE)

(*) Notice: Subject to any disclaimer, the term of this patent is extended or adjusted under 35 U.S.C. 154(b) by 201 days.

(21) Appl. No.: 15/830,225

(22) Filed: Dec. 4, 2017

(65) Prior Publication Data

US 2018/0230486 A1 Aug. 16, 2018

Related U.S. Application Data

(62) Division of application No. 13/881,592, filed as application No. PCT/EP2011/005400 on Oct. 26, 2011, now Pat. No. 9,862,968.

(30) Foreign Application Priority Data

Oct. 26, 2010 (EP) ..................................... 10188893

(51) Int. Cl.
*C12N 15/85* (2006.01)
*C12N 5/0784* (2010.01)
*C12N 9/12* (2006.01)
*A61K 35/12* (2015.01)
*A61K 39/00* (2006.01)

(52) U.S. Cl.
CPC ............. *C12N 15/85* (2013.01); *C12N 5/064* (2013.01); *C12N 9/1205* (2013.01); *A61K 2035/122* (2013.01); *A61K 2039/5154* (2013.01); *C12N 2501/70* (2013.01); *C12N 2510/00* (2013.01)

(58) Field of Classification Search
None
See application file for complete search history.

(56) References Cited

U.S. PATENT DOCUMENTS

| | | | |
|---|---|---|---|
| 2005/0059634 A1* | 3/2005 | Venton | C08B 37/0012 514/58 |
| 2009/0202492 A1* | 8/2009 | Beg | C12N 9/1205 424/93.2 |

OTHER PUBLICATIONS

Mercurio et al., 1997, Science vol. 278: 860-866.*
Delhase et al., 1999, Science, vol. 284: 309-313.*

* cited by examiner

*Primary Examiner* — Amy E Juedes
(74) *Attorney, Agent, or Firm* — Daniel A. Rosenberg; Taft Stettinius & Hollister LLP

(57) ABSTRACT

The invention relates to dendritic cells, the NFκB signaling pathway of which has been manipulated by RNA transfection, to the manufacture thereof and to use thereof.

16 Claims, 14 Drawing Sheets

Specification includes a Sequence Listing.

□ naïve T cells   ■ central memory cells   ■ effector memory cells   ▣ lytic effector cells

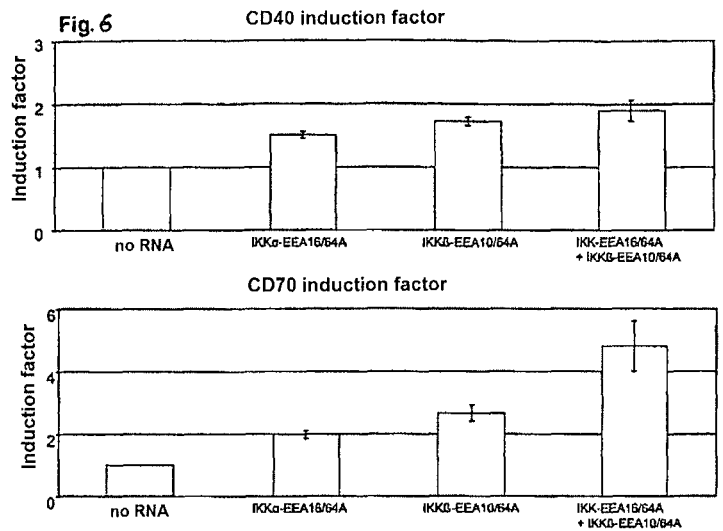
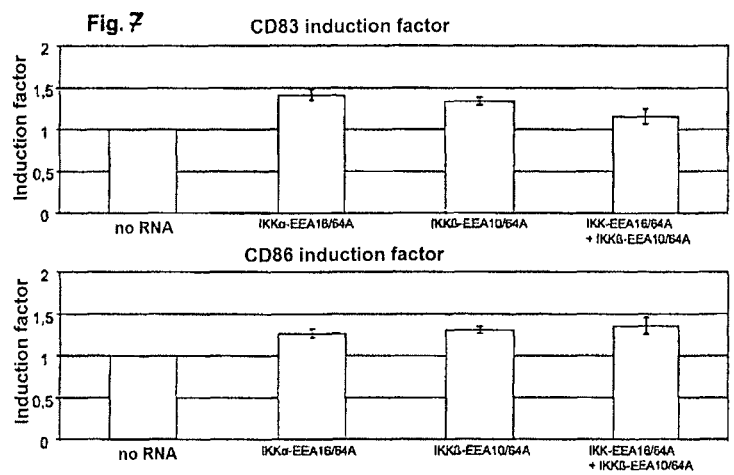

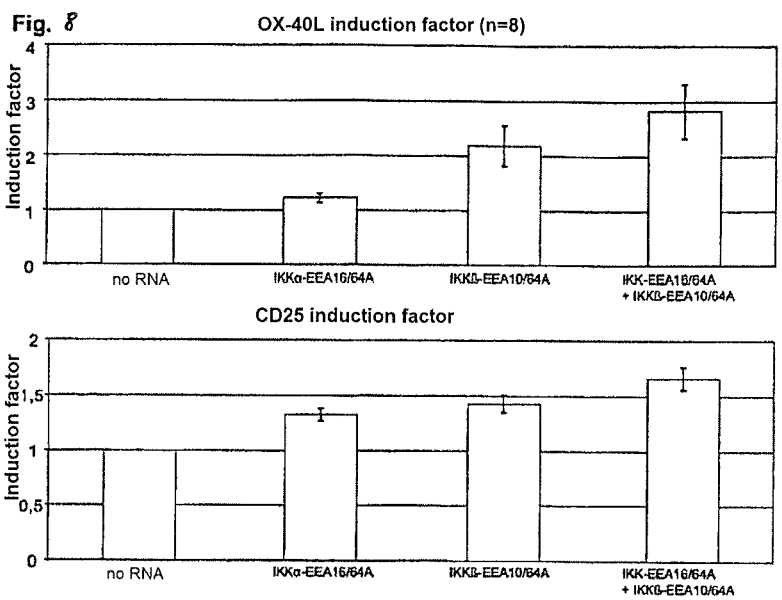
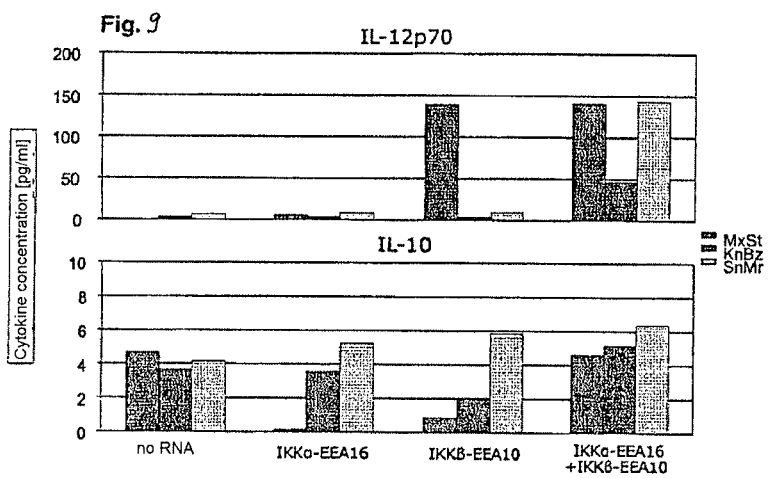

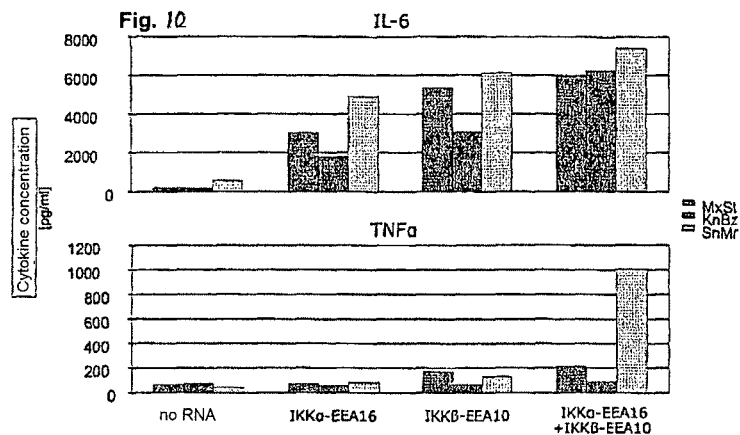
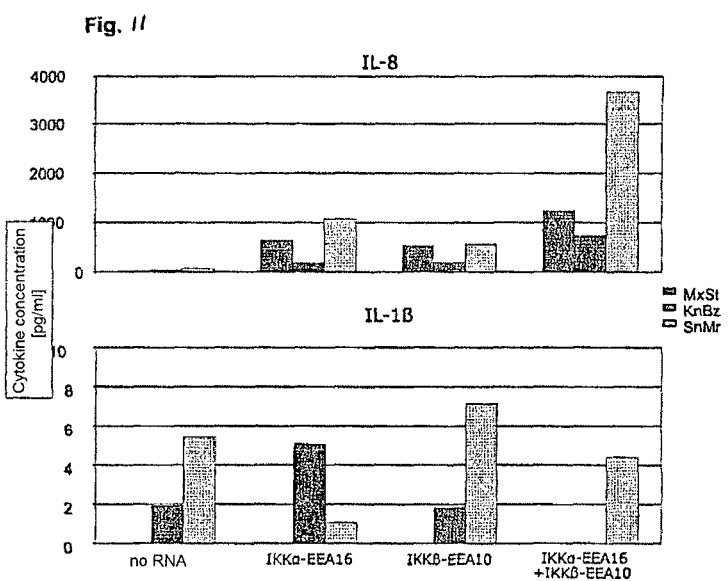

SEQUENCE LISTING

<160> NUMBER OF SEQ ID NOS: 10

<210> SEQ ID NO 1
<211> LENGTH: 745
<212> TYPE: PRT
<213> ORGANISM: Homo sapiens

<400> SEQUENCE: 1

Met Glu Arg Pro Pro Gly Leu Arg Pro Gly Ala Gly Gly Pro Trp Glu
1               5                   10                  15

Met Arg Glu Arg Leu Gly Thr Gly Gly Phe Gly Asn Val Cys Leu Tyr
            20                  25                  30

Gln His Arg Glu Leu Asp Leu Lys Ile Ala Ile Lys Ser Cys Arg Leu
        35                  40                  45

Glu Leu Ser Thr Lys Asn Arg Glu Arg Trp Cys His Glu Ile Gln Ile
    50                  55                  60

Met Lys Lys Leu Asn His Ala Asn Val Val Lys Ala Cys Asp Val Pro
65                  70                  75                  80

Glu Glu Leu Asn Ile Leu Ile His Asp Val Pro Leu Leu Ala Met Glu
                85                  90                  95

Tyr Cys Ser Gly Gly Asp Leu Arg Lys Leu Leu Asn Lys Pro Glu Asn
            100                 105                 110

Cys Cys Gly Leu Lys Glu Ser Gln Ile Leu Ser Leu Leu Ser Asp Ile
        115                 120                 125

Gly Ser Gly Ile Arg Tyr Leu His Glu Asn Lys Ile Ile His Arg Asp
    130                 135                 140

Leu Lys Pro Glu Asn Ile Val Leu Gln Asp Val Gly Gly Lys Ile Ile
145                 150                 155                 160

His Lys Ile Ile Asp Leu Gly Tyr Ala Lys Asp Val Asp Gln Gly Ser
                165                 170                 175

Leu Cys Thr Ser Phe Val Gly Thr Leu Gln Tyr Leu Ala Pro Glu Leu
            180                 185                 190

Phe Glu Asn Lys Pro Tyr Thr Ala Thr Val Asp Tyr Trp Ser Phe Gly
        195                 200                 205

Thr Met Val Phe Glu Cys Ile Ala Gly Tyr Arg Pro Phe Leu His His
    210                 215                 220

Leu Gln Pro Phe Thr Trp His Glu Lys Ile Lys Lys Lys Asp Pro Lys
225                 230                 235                 240

Cys Ile Phe Ala Cys Glu Glu Met Ser Gly Glu Val Arg Phe Ser Ser
                245                 250                 255

His Leu Pro Gln Pro Asn Ser Leu Cys Ser Leu Ile Val Glu Pro Met
            260                 265                 270

Glu Asn Trp Leu Gln Leu Met Leu Asn Trp Asp Pro Gln Gln Arg Gly
        275                 280                 285

Gly Pro Val Asp Leu Thr Leu Lys Gln Pro Arg Cys Phe Val Leu Met
    290                 295                 300

Asp His Ile Leu Asn Leu Lys Ile Val His Ile Leu Asn Met Thr Ser
305                 310                 315                 320

Ala Lys Ile Ile Ser Phe Leu Leu Pro Pro Asp Glu Ser Leu His Ser
                325                 330                 335

Leu Gln Ser Arg Ile Glu Arg Glu Thr Gly Ile Asn Thr Gly Ser Gln
            340                 345                 350

Glu Leu Leu Ser Glu Thr Gly Ile Ser Leu Asp Pro Arg Lys Pro Ala
        355                 360                 365

Ser Gln Cys Val Leu Asp Gly Val Arg Gly Cys Asp Ser Tyr Met Val
    370                 375                 380

Tyr Leu Phe Asp Lys Ser Lys Thr Val Tyr Glu Gly Pro Phe Ala Ser
385                 390                 395                 400

Arg Ser Leu Ser Asp Cys Val Asn Tyr Ile Val Gln Asp Ser Lys Ile
                405                 410                 415

Gln Leu Pro Ile Ile Gln Leu Arg Lys Val Trp Ala Glu Ala Val His
            420                 425                 430

Tyr Val Ser Gly Leu Lys Glu Asp Tyr Ser Arg Leu Phe Gln Gly Gln
        435                 440                 445

Arg Ala Ala Met Leu Ser Leu Leu Arg Tyr Asn Ala Asn Leu Thr Lys
450                 455                 460

Met Lys Asn Thr Leu Ile Ser Ala Ser Gln Gln Leu Lys Ala Lys Leu
465                 470                 475                 480

Glu Phe Phe His Lys Ser Ile Gln Leu Asp Leu Glu Arg Tyr Ser Glu
                485                 490                 495

Gln Met Thr Tyr Gly Ile Ser Ser Glu Lys Met Leu Lys Ala Trp Lys
            500                 505                 510

Glu Met Glu Glu Lys Ala Ile His Tyr Ala Glu Val Gly Val Ile Gly
        515                 520                 525

Tyr Leu Glu Asp Gln Ile Met Ser Leu His Ala Glu Ile Met Glu Leu
530                 535                 540

Gln Lys Ser Pro Tyr Gly Arg Arg Gln Gly Asp Leu Met Glu Ser Leu
545                 550                 555                 560

Glu Gln Arg Ala Ile Asp Leu Tyr Lys Gln Leu Lys His Arg Pro Ser
                565                 570                 575

Asp His Ser Tyr Ser Asp Ser Thr Glu Met Val Lys Ile Ile Val His
            580                 585                 590

Thr Val Gln Ser Gln Asp Arg Val Leu Lys Glu Leu Phe Gly His Leu
        595                 600                 605

Ser Lys Leu Leu Gly Cys Lys Gln Lys Ile Ile Asp Leu Leu Pro Lys
610                 615                 620

Val Glu Val Ala Leu Ser Asn Ile Lys Glu Ala Asp Asn Thr Val Met
625                 630                 635                 640

Phe Met Gln Gly Lys Arg Gln Lys Glu Ile Trp His Leu Leu Lys Ile
                645                 650                 655

Ala Cys Thr Gln Ser Ser Ala Arg Ser Leu Val Gly Ser Ser Leu Glu
            660                 665                 670

Gly Ala Val Thr Pro Gln Thr Ser Ala Trp Leu Pro Pro Thr Ser Ala
        675                 680                 685

Glu His Asp His Ser Leu Ser Cys Val Val Thr Pro Gln Asp Gly Glu
690                 695                 700

Thr Ser Ala Gln Met Ile Glu Glu Asn Leu Asn Cys Leu Gly His Leu
705                 710                 715                 720

Ser Thr Ile Ile His Glu Ala Asn Glu Glu Gln Gly Asn Ser Met Met
                725                 730                 735

Asn Leu Asp Trp Ser Trp Leu Thr Glu
            740                 745

<210> SEQ ID NO 2
<211> LENGTH: 769
<212> TYPE: PRT
<213> ORGANISM: Artificial
<220> FEATURE:
<223> OTHER INFORMATION: IKK-alpha Constitutively Active Mutant

<400> SEQUENCE: 2

```
His His His His His Gly Asp Tyr Lys Asp Asp Asp Lys Gly Asp
1               5                   10                  15

Ile Glu Gly Arg Gly His Met Thr Met Glu Arg Pro Pro Gly Leu Arg
                20                  25                  30

Pro Gly Ala Gly Gly Pro Trp Glu Met Arg Glu Arg Leu Gly Thr Gly
            35                  40                  45

Gly Phe Gly Asn Val Cys Leu Tyr Gln His Arg Glu Leu Asp Leu Lys
    50                  55                  60

Ile Ala Ile Lys Ser Cys Arg Leu Glu Leu Ser Thr Lys Asn Arg Glu
65                  70                  75                  80

Arg Trp Cys His Glu Ile Gln Ile Met Lys Lys Leu Asn His Ala Asn
                85                  90                  95

Val Val Lys Ala Cys Asp Val Pro Glu Glu Leu Asn Ile Leu Ile His
            100                 105                 110

Asp Val Pro Leu Leu Ala Met Glu Tyr Cys Ser Gly Gly Asp Leu Arg
        115                 120                 125

Lys Leu Leu Asn Lys Pro Glu Asn Cys Cys Gly Leu Lys Glu Ser Gln
    130                 135                 140

Ile Leu Ser Leu Leu Ser Asp Ile Gly Ser Gly Ile Arg Tyr Leu His
145                 150                 155                 160

Glu Asn Lys Ile Ile His Arg Asp Leu Lys Pro Glu Asn Ile Val Leu
                165                 170                 175

Gln Asp Val Gly Gly Lys Ile Ile His Lys Ile Asp Leu Gly Tyr
            180                 185                 190

Ala Lys Asp Val Asp Gln Gly Glu Leu Cys Thr Glu Phe Val Gly Thr
        195                 200                 205

Leu Gln Tyr Leu Ala Pro Glu Leu Phe Glu Asn Lys Pro Tyr Thr Ala
    210                 215                 220

Thr Val Asp Tyr Trp Ser Phe Gly Thr Met Val Phe Glu Cys Ile Ala
225                 230                 235                 240

Gly Tyr Arg Pro Phe Leu His His Leu Gln Pro Phe Thr Trp His Glu
                245                 250                 255

Lys Ile Lys Lys Lys Asp Pro Lys Cys Ile Phe Ala Cys Glu Glu Met
            260                 265                 270

Ser Gly Glu Val Arg Phe Ser Ser His Leu Pro Gln Pro Asn Ser Leu
        275                 280                 285

Cys Ser Leu Ile Val Glu Pro Met Glu Asn Trp Leu Gln Leu Met Leu
    290                 295                 300

Asn Trp Asp Pro Gln Gln Arg Gly Gly Pro Val Asp Leu Thr Leu Lys
305                 310                 315                 320

Gln Pro Arg Cys Phe Val Leu Met Asp His Ile Leu Asn Leu Lys Ile
                325                 330                 335

Val His Ile Leu Asn Met Thr Ser Ala Lys Ile Ile Ser Phe Leu Leu
            340                 345                 350

Pro Pro Asp Glu Ser Leu His Ser Leu Gln Ser Arg Ile Glu Arg Glu
        355                 360                 365

Thr Gly Ile Asn Thr Gly Ser Gln Glu Leu Leu Ser Glu Thr Gly Ile
    370                 375                 380

Ser Leu Asp Pro Arg Lys Pro Ala Ser Gln Cys Val Leu Asp Gly Val
385                 390                 395                 400

Arg Gly Cys Asp Ser Tyr Met Val Tyr Leu Phe Asp Lys Ser Lys Thr
```

```
            405                 410                 415
Val Tyr Glu Gly Pro Phe Ala Ser Arg Ser Leu Ser Asp Cys Val Asn
            420                 425                 430

Tyr Ile Val Gln Asp Ser Lys Ile Gln Leu Pro Ile Ile Gln Leu Arg
            435                 440                 445

Lys Ala Trp Ala Glu Ala Val His Tyr Val Ser Gly Leu Lys Glu Asp
450                 455                 460

Tyr Ser Arg Leu Phe Gln Gly Gln Arg Ala Ala Met Leu Ser Leu Leu
465                 470                 475                 480

Arg Tyr Asn Ala Asn Leu Thr Lys Met Lys Asn Thr Leu Ile Ser Ala
            485                 490                 495

Ser Gln Gln Leu Lys Ala Lys Leu Glu Phe Phe His Lys Ser Ile Gln
            500                 505                 510

Leu Asp Leu Glu Arg Tyr Ser Glu Gln Met Thr Tyr Gly Ile Ser Ser
            515                 520                 525

Glu Lys Met Leu Lys Ala Trp Lys Glu Met Glu Glu Lys Ala Ile His
            530                 535                 540

Tyr Ala Glu Val Gly Val Ile Gly Tyr Leu Glu Asp Gln Ile Met Ser
545                 550                 555                 560

Leu His Ala Glu Ile Met Glu Leu Gln Lys Ser Pro Tyr Gly Arg Arg
            565                 570                 575

Gln Gly Asp Leu Met Glu Ser Leu Glu Gln Arg Ala Ile Asp Leu Tyr
            580                 585                 590

Lys Gln Leu Lys His Arg Pro Ser Asp His Ser Tyr Ser Asp Ser Thr
            595                 600                 605

Glu Met Val Lys Ile Ile Val His Thr Val Gln Ser Gln Asp Arg Val
610                 615                 620

Leu Lys Glu Leu Phe Gly His Leu Ser Lys Leu Leu Gly Cys Lys Gln
625                 630                 635                 640

Lys Ile Ile Asp Leu Leu Pro Lys Val Glu Val Ala Leu Ser Asn Ile
            645                 650                 655

Lys Glu Ala Asp Asn Thr Val Met Phe Met Gln Gly Lys Arg Gln Lys
            660                 665                 670

Glu Ile Trp His Leu Leu Lys Ile Ala Cys Thr Gln Ala Ala Ala Arg
            675                 680                 685

Ala Leu Val Gly Ala Ala Leu Glu Gly Ala Val Ala Pro Gln Ala Ala
            690                 695                 700

Ala Trp Leu Pro Pro Ala Ala Ala Glu His Asp His Ala Leu Ala Cys
705                 710                 715                 720

Val Val Ala Pro Gln Asp Gly Glu Ala Ala Gln Met Ile Glu Glu
            725                 730                 735

Asn Leu Asn Cys Leu Gly His Leu Ala Ala Ile Ile His Glu Ala Asn
            740                 745                 750

Glu Glu Gln Gly Asn Ser Met Met Asn Leu Asp Trp Ser Trp Leu Thr
            755                 760                 765

Glu

<210> SEQ ID NO 3
<211> LENGTH: 2238
<212> TYPE: DNA
<213> ORGANISM: Artificial
<220> FEATURE:
<223> OTHER INFORMATION: IKK-alpha Constitutively Active Mutant

<400> SEQUENCE: 3
```

```
atggagcggc cccgggggct gcggccgggc gcggcggggc cctgggagat gcgggagcgg      60
ctgggcaccg gcggcttcgg gaacgtctgt ctgtaccagc atcgggaact tgatctcaaa     120
atagcaatta agtcttgtcg cctagagcta agtaccaaaa acagagaacg atggtgccat     180
gaaatccaga ttatgaagaa gttgaaccat gccaatgttg taaaggcctg tgatgttcct     240
gaagaattga atattttgat tcatgatgtg cctcttctag caatggaata ctgttctgga     300
ggagatctcc gaaagctgct caacaaacca gaaaattgtt gtggacttaa agaaagccag     360
atactttctt tactaagtga tatagggtct gggattcgat atttgcatga aaacaaaatt     420
atacatcgag atctaaaacc tgaaaacata gttcttcagg atgttggtgg aaagataata     480
cataaaataa ttgatctggg atatgccaaa gatgttgatc aaggagagct gtgtacagag     540
tttgtgggaa cactgcagta tctggcccca gagctctttg agaataagcc ttacacagcc     600
actgttgatt attggagctt tgggaccatg gtatttgaat gtattgctgg atataggcct     660
tttttgcatc atctgcagcc atttacctgg catgagaaga ttaagaagaa ggatccaaag     720
tgtatatttg catgtgaaga gatgtcagga gaagttcggt ttagtagcca tttacctcaa     780
ccaaatagcc tttgtagttt aatagtagaa cccatggaaa actggctaca gttgatgttg     840
aattgggacc ctcagcagag aggaggacct gttgacctta ctttgaagca gccaagatgt     900
tttgtattaa tggatcacat tttgaatttg aagatagtac acatcctaaa tatgacttct     960
gcaaagataa tttctttctt gttaccacct gatgaaagtc ttcattcatt acagtctcgt    1020
attgagcgtg aaactggaat aaatactggt tctcaagaac ttctttcaga gacaggaatt    1080
tctctggatc ctcggaaacc agcctctcaa tgtgttctag atggagttag aggctgtgat    1140
agctatatgg tttatttgtt tgataaaagt aaaactgtat atgaagggcc atttgcttcc    1200
agaagtttat ctgattgtgt aaattatatt gtacaggaca gcaaaataca gcttccaatt    1260
atacagctgc gtaaagcgtg ggctgaagca gtgcactatg tgtctggact aaaagaagac    1320
tatagcaggc tctttcaggg acaaagggca gcaatgttaa gtcttcttag atataatgct    1380
aacttaacaa aaatgaagaa cactttgatc tcagcatcac aacaactgaa agctaaattg    1440
gagttttttc acaaaagcat tcagcttgac ttggagagat acagcgagca gatgacgtat    1500
gggatatctt cagaaaaaat gctaaaagca tggaaagaaa tggaagaaaa ggccatccac    1560
tatgctgagg ttggtgtcat tggatacctg gaggatcaga ttatgtcttt gcatgctgaa    1620
atcatggagc tacagaagag cccctatgga agacgtcagg gagacttgat ggaatctctg    1680
gaacagcgtg ccattgatct atataagcag ttaaaacaca gaccttcaga tcactcctac    1740
agtgacagca gagatggt gaaaatcatt gtgcacactg tgcagagtca ggaccgtgtg    1800
ctcaaggagc tgtttggtca tttgagcaag ttgttgggct gtaagcagaa gattattgat    1860
ctactcccta aggtggaagt ggccctcagt aatatcaaag aagctgacaa tactgtcatg    1920
ttcatgcagg aaaaaggca gaaagaaatc tggcatctcc ttaaaattgc ctgtacacag    1980
gccgctgccc gcgcccttgt gggagccgct ctggaaggtg cagtggcccc acaggccgcc    2040
gcatggctgc cccctgctgc cgcagaacac gatcacgctc tggcctgtgt ggtggctcct    2100
caagatgggg aggctgccgc acaaatgatc gaagaaaatt tgaactgcct tggccacttg    2160
gccgctatta ttcacgaggc aaatgaggaa cagggcaata gtatgatgaa tcttgattgg    2220
agttggttga cagaatga                                                  2238
```

<210> SEQ ID NO 4

```
<211> LENGTH: 756
<212> TYPE: PRT
<213> ORGANISM: Homo sapiens

<400> SEQUENCE: 4

Met Ser Trp Ser Pro Ser Leu Thr Thr Gln Thr Cys Gly Ala Trp Glu
1               5                   10                  15

Met Lys Glu Arg Leu Gly Thr Gly Gly Phe Gly Asn Val Ile Arg Trp
            20                  25                  30

His Asn Gln Glu Thr Gly Glu Gln Ile Ala Ile Lys Gln Cys Arg Gln
        35                  40                  45

Glu Leu Ser Pro Arg Asn Arg Glu Arg Trp Cys Leu Glu Ile Gln Ile
50                  55                  60

Met Arg Arg Leu Thr His Pro Asn Val Val Ala Ala Arg Asp Val Pro
65                  70                  75                  80

Glu Gly Met Gln Asn Leu Ala Pro Asn Asp Leu Pro Leu Leu Ala Met
                85                  90                  95

Glu Tyr Cys Gln Gly Gly Asp Leu Arg Lys Tyr Leu Asn Gln Phe Glu
            100                 105                 110

Asn Cys Cys Gly Leu Arg Glu Gly Ala Ile Leu Thr Leu Leu Ser Asp
        115                 120                 125

Ile Ala Ser Ala Leu Arg Tyr Leu His Glu Asn Arg Ile Ile His Arg
130                 135                 140

Asp Leu Lys Pro Glu Asn Ile Val Leu Gln Gln Gly Glu Gln Arg Leu
145                 150                 155                 160

Ile His Lys Ile Ile Asp Leu Gly Tyr Ala Lys Glu Leu Asp Gln Gly
                165                 170                 175

Ser Leu Cys Thr Ser Phe Val Gly Thr Leu Gln Tyr Leu Ala Pro Glu
            180                 185                 190

Leu Leu Glu Gln Gln Lys Tyr Thr Val Thr Val Asp Tyr Trp Ser Phe
        195                 200                 205

Gly Thr Leu Ala Phe Glu Cys Ile Thr Gly Phe Arg Pro Phe Leu Pro
210                 215                 220

Asn Trp Gln Pro Val Gln Trp His Ser Lys Val Arg Gln Lys Ser Glu
225                 230                 235                 240

Val Asp Ile Val Val Ser Glu Asp Leu Asn Gly Thr Val Lys Phe Ser
                245                 250                 255

Ser Ser Leu Pro Tyr Pro Asn Asn Leu Asn Ser Val Leu Ala Glu Arg
            260                 265                 270

Leu Glu Lys Trp Leu Gln Leu Met Leu Met Trp His Pro Arg Gln Arg
        275                 280                 285

Gly Thr Asp Pro Thr Tyr Gly Pro Asn Gly Cys Phe Lys Ala Leu Asp
290                 295                 300

Asp Ile Leu Asn Leu Lys Leu Val His Ile Leu Asn Met Val Thr Gly
305                 310                 315                 320

Thr Ile His Thr Tyr Pro Val Thr Glu Asp Glu Ser Leu Gln Ser Leu
                325                 330                 335

Lys Ala Arg Ile Gln Gln Asp Thr Gly Ile Pro Glu Glu Asp Gln Glu
            340                 345                 350

Leu Leu Gln Glu Ala Gly Leu Ala Leu Ile Pro Asp Lys Pro Ala Thr
        355                 360                 365

Gln Cys Ile Ser Asp Gly Lys Leu Asn Glu Gly His Thr Leu Asp Met
370                 375                 380

Asp Leu Val Phe Leu Phe Asp Asn Ser Lys Ile Thr Tyr Glu Thr Gln
```

```
                385                 390                 395                 400
        Ile Ser Pro Arg Pro Gln Pro Glu Ser Val Ser Cys Ile Leu Gln Glu
                        405                 410                 415

Pro Lys Arg Asn Leu Ala Phe Phe Gln Leu Arg Lys Val Trp Gly Gln
                        420                 425                 430

Val Trp His Ser Ile Gln Thr Leu Lys Glu Asp Cys Asn Arg Leu Gln
                        435                 440                 445

Gln Gly Gln Arg Ala Ala Met Met Asn Leu Leu Arg Asn Asn Ser Cys
                450                 455                 460

Leu Ser Lys Met Lys Asn Ser Met Ala Ser Met Ser Gln Gln Leu Lys
        465                 470                 475                 480

Ala Lys Leu Asp Phe Phe Lys Thr Ser Ile Gln Ile Asp Leu Glu Lys
                        485                 490                 495

Tyr Ser Glu Gln Thr Glu Phe Gly Ile Thr Ser Asp Lys Leu Leu Leu
                        500                 505                 510

Ala Trp Arg Glu Met Glu Gln Ala Val Glu Leu Cys Gly Arg Glu Asn
                        515                 520                 525

Glu Val Lys Leu Leu Val Glu Arg Met Met Ala Leu Gln Thr Asp Ile
                530                 535                 540

Val Asp Leu Gln Arg Ser Pro Met Gly Arg Lys Gln Gly Gly Thr Leu
        545                 550                 555                 560

Asp Asp Leu Glu Glu Gln Ala Arg Glu Leu Tyr Arg Arg Leu Arg Glu
                        565                 570                 575

Lys Pro Arg Asp Gln Arg Thr Glu Gly Asp Ser Gln Glu Met Val Arg
                        580                 585                 590

Leu Leu Leu Gln Ala Ile Gln Ser Phe Glu Lys Lys Val Arg Val Ile
                        595                 600                 605

Tyr Thr Gln Leu Ser Lys Thr Val Val Cys Lys Gln Lys Ala Leu Glu
                        610                 615                 620

Leu Leu Pro Lys Val Glu Glu Val Val Ser Leu Met Asn Glu Asp Glu
        625                 630                 635                 640

Lys Thr Val Val Arg Leu Gln Glu Lys Arg Gln Lys Glu Leu Trp Asn
                        645                 650                 655

Leu Leu Lys Ile Ala Cys Ser Lys Val Arg Gly Pro Val Ser Gly Ser
                        660                 665                 670

Pro Asp Ser Met Asn Ala Ser Arg Leu Ser Gln Pro Gly Gln Leu Met
                        675                 680                 685

Ser Gln Pro Ser Thr Ala Ser Asn Ser Leu Pro Glu Pro Ala Lys Lys
                690                 695                 700

Ser Glu Glu Leu Val Ala Glu Ala His Asn Leu Cys Thr Leu Leu Glu
        705                 710                 715                 720

Asn Ala Ile Gln Asp Thr Val Arg Glu Gln Asp Gln Ser Phe Thr Ala
                        725                 730                 735

Leu Asp Trp Ser Trp Leu Gln Thr Glu Glu Glu His Ser Cys Leu
                        740                 745                 750

Glu Gln Ala Ser
                755

<210> SEQ ID NO 5
<211> LENGTH: 773
<212> TYPE: PRT
<213> ORGANISM: Artificial
<220> FEATURE:
<223> OTHER INFORMATION: IKK-beta Constitutively Active Mutant
```

<400> SEQUENCE: 5

```
Met Asp Tyr Lys Asp Asp Asp Lys Gly Asp Ile Glu Gly Arg Gly
1               5                   10                  15

His Met Ser Trp Ser Pro Ser Leu Thr Thr Gln Thr Cys Gly Ala Trp
            20                  25                  30

Glu Met Lys Glu Arg Leu Gly Thr Gly Gly Phe Gly Asn Val Ile Arg
        35                  40                  45

Trp His Asn Gln Glu Thr Gly Glu Gln Ile Ala Ile Lys Gln Cys Arg
        50                  55                  60

Gln Glu Leu Ser Pro Arg Asn Arg Glu Arg Trp Cys Leu Glu Ile Gln
65                  70                  75                  80

Ile Met Arg Arg Leu Thr His Pro Asn Val Val Ala Ala Arg Asp Val
                85                  90                  95

Pro Glu Gly Met Gln Asn Leu Ala Pro Asn Asp Leu Pro Leu Leu Ala
            100                 105                 110

Met Glu Tyr Cys Gln Gly Gly Asp Leu Arg Lys Tyr Leu Asn Gln Phe
        115                 120                 125

Glu Asn Cys Cys Gly Leu Arg Glu Gly Ala Ile Leu Thr Leu Leu Ser
    130                 135                 140

Asp Ile Ala Ser Ala Leu Arg Tyr Leu His Glu Asn Arg Ile Ile His
145                 150                 155                 160

Arg Asp Leu Lys Pro Glu Asn Ile Val Leu Gln Gln Gly Glu Gln Arg
                165                 170                 175

Leu Ile His Lys Ile Ile Asp Leu Gly Tyr Ala Lys Glu Leu Asp Gln
            180                 185                 190

Gly Glu Leu Cys Thr Glu Phe Val Gly Thr Leu Gln Tyr Leu Ala Pro
        195                 200                 205

Glu Leu Leu Glu Gln Gln Lys Tyr Thr Val Thr Val Asp Tyr Trp Ser
    210                 215                 220

Phe Gly Thr Leu Ala Phe Glu Cys Ile Thr Gly Phe Arg Pro Phe Leu
225                 230                 235                 240

Pro Asn Trp Gln Pro Val Gln Trp His Ser Lys Val Arg Gln Lys Ser
                245                 250                 255

Glu Val Asp Ile Val Val Ser Glu Asp Leu Asn Gly Thr Val Lys Phe
            260                 265                 270

Ser Ser Ser Leu Pro Tyr Pro Asn Asn Leu Asn Ser Val Leu Ala Glu
        275                 280                 285

Arg Leu Glu Lys Trp Leu Gln Leu Met Leu Met Trp His Pro Arg Gln
    290                 295                 300

Arg Gly Thr Asp Pro Thr Tyr Gly Pro Asn Gly Cys Phe Lys Ala Leu
305                 310                 315                 320

Asp Asp Ile Leu Asn Leu Lys Leu Val His Ile Leu Asn Met Val Thr
                325                 330                 335

Gly Thr Ile His Thr Tyr Pro Val Thr Glu Asp Glu Ser Leu Gln Ser
            340                 345                 350

Leu Lys Ala Arg Ile Gln Gln Asp Thr Gly Ile Pro Glu Glu Asp Gln
        355                 360                 365

Glu Leu Leu Gln Glu Ala Gly Leu Ala Leu Ile Pro Asp Lys Pro Ala
    370                 375                 380

Thr Gln Cys Ile Ser Asp Gly Lys Leu Asn Glu Gly His Thr Leu Asp
385                 390                 395                 400

Met Asp Leu Val Phe Leu Phe Asp Asn Ser Lys Ile Thr Tyr Glu Thr
                405                 410                 415
```

Gln Ile Ser Pro Arg Pro Gln Pro Glu Ser Val Ser Cys Ile Leu Gln
            420                 425                 430

Glu Pro Lys Arg Asn Leu Ala Phe Phe Gln Leu Arg Lys Val Trp Gly
            435                 440                 445

Gln Val Trp His Ser Ile Gln Thr Leu Lys Glu Asp Cys Asn Arg Leu
        450                 455                 460

Gln Gln Gly Gln Arg Ala Ala Met Met Asn Leu Leu Arg Asn Asn Ser
465                 470                 475                 480

Cys Leu Ser Lys Met Lys Asn Ser Met Ala Ser Met Ser Gln Gln Leu
                485                 490                 495

Lys Ala Lys Leu Asp Phe Phe Lys Thr Ser Ile Gln Ile Asp Leu Glu
            500                 505                 510

Lys Tyr Ser Glu Gln Thr Glu Phe Gly Ile Thr Ser Asp Lys Leu Leu
        515                 520                 525

Leu Ala Trp Arg Glu Met Glu Gln Ala Val Glu Leu Cys Gly Arg Glu
            530                 535                 540

Asn Glu Val Lys Leu Leu Val Glu Arg Met Met Ala Leu Gln Thr Asp
545                 550                 555                 560

Ile Val Asp Leu Gln Arg Ser Pro Met Gly Arg Lys Gln Gly Gly Thr
                565                 570                 575

Leu Asp Asp Leu Glu Glu Gln Ala Arg Glu Leu Tyr Arg Arg Leu Arg
            580                 585                 590

Glu Lys Pro Arg Asp Gln Arg Thr Glu Gly Asp Ser Gln Glu Met Val
        595                 600                 605

Arg Leu Leu Leu Gln Ala Ile Gln Ser Phe Glu Lys Lys Val Arg Val
            610                 615                 620

Ile Tyr Thr Gln Leu Ser Lys Thr Val Val Cys Lys Gln Lys Ala Leu
625                 630                 635                 640

Glu Leu Leu Pro Lys Val Glu Val Val Ser Leu Met Asn Glu Asp
                645                 650                 655

Glu Lys Thr Val Val Arg Leu Gln Glu Lys Arg Gln Lys Glu Leu Trp
            660                 665                 670

Asn Leu Leu Lys Ile Ala Cys Ser Lys Val Arg Gly Pro Val Ala Gly
        675                 680                 685

Ala Pro Asp Ala Met Asn Ala Ala Arg Leu Ala Gln Pro Gly Gln Leu
            690                 695                 700

Met Ala Gln Pro Ala Thr Ala Ala Asn Ala Leu Pro Glu Pro Ala Lys
705                 710                 715                 720

Lys Ala Glu Glu Leu Val Ala Glu Ala His Asn Leu Cys Thr Leu Leu
                725                 730                 735

Glu Asn Ala Ile Gln Asp Thr Val Arg Glu Gln Asp Gln Ser Phe Thr
            740                 745                 750

Ala Leu Asp Trp Ser Trp Leu Gln Thr Glu Glu Glu His Ser Cys
        755                 760                 765

Leu Glu Gln Ala Ser
    770

<210> SEQ ID NO 6
<211> LENGTH: 2319
<212> TYPE: DNA
<213> ORGANISM: Artificial
<220> FEATURE:
<223> OTHER INFORMATION: IKK-beta Constitutively Active Mutant

<400> SEQUENCE: 6

-continued

```
atggactaca aggacgacga tgacaaaggt gacatcgaag gtagaggtca tatgagctgg      60
tcaccttccc tgacaacgca gacatgcggg gcctgggaaa tgaaagagcg ccttgggaca     120
gggggatttg gaaatgtcat ccgatggcac aatcaggaaa caggtgagca gattgccatc     180
aagcagtgcc ggcaggagct cagcccccgg aaccgagagc ggtggtgcct ggagatccag     240
atcatgagaa ggctgaccca ccccaatgtg gtggctgccc gagatgtccc tgagggatg     300 cagaacttgg cgcccaatga cctgcccctg ctggccatgg agtactgcca aggaggagat     360
ctccggaagt acctgaacca gtttgagaac tgctgtggtc tgcgggaagg tgccatcctc     420
accttgctga gtgacattgc ctctgcgctt agataccttc atgaaaacag aatcatccat     480
cgggatctaa agccagaaaa catcgtcctg cagcaaggag aacagaggtt aatacacaaa     540
attattgacc taggatatgc caaggagctg atcagggcg agctttgcac agagttcgtg     600
gggaccctgc agtacctggc cccagagcta ctggagcagc agaagtacac agtgaccgtc     660
gactactgga gcttcggcac cctggccttt gagtgcatca cgggcttccg gcccttcctc     720
cccaactggc agcccgtgca gtggcattca aaagtgcggc agaagagtga ggtggacatt     780
gttgttagcg aagacttgaa tggaacggtg aagttttcaa gctctttacc ctaccccaat     840
aatcttaaca gtgtcctggc tgagcgactg agaagtggc tgcaactgat gctgatgtgg     900
cacccccgac agaggggcac ggatcccacg tatgggccca atggctgctt caaggccctg     960
gatgacatct taaacttaaa gctggttcat atcttgaaca tggtcacggg caccatccac    1020
acctaccctg tgacagagga tgagagtctg cagagcttga aggccagaat ccaacaggac    1080
acgggcatcc cagaggagga ccaggagctg ctgcaggaag cgggcctggc gttgatcccc    1140
gataagcctg ccactcagtg tatttcagac ggcaagttaa atgagggcca cacattggac    1200
atggatcttg tttttctctt tgacaacagt aaaatcacct atgagactca gatctcccca    1260
cggccccaac ctgaaagtgt cagctgtatc cttcaagagc ccaagaggaa tctcgccttc    1320
ttccagctga ggaaggtgtg gggccaggtc tggcacagca tccagaccct gaaggaagat    1380
tgcaaccggc tgcagcaggg acagcgagcc gccatgatga atctcctccg aaacaacagc    1440
tgcctctcca aaatgaagaa ttccatggct tccatgtctc agcagctcaa ggccaagttg    1500
gatttcttca aaaccagcat ccagattgac ctggagaagt acagcgagca aaccgagttt    1560
gggatcacat cagataaact gctgctggcc tggaggaaa tggagcaggc tgtgagctc    1620 tgtgggcggg agaacgaagt gaaactcctg gtagaacgga tgatggctct gcagaccgac    1680
attgtggact acagaggag ccccatgggc cggaagcagg gggaacgct ggacgaccta    1740 gaggagcaag caagggagct gtacaggaga ctaagggaaa aacctcgaga ccagcgaact    1800
gagggtgaca gtcaggaaat ggtacggctg ctgcttcagg caattcagag cttcgagaag    1860
aaagtgcgag tgatctatac gcagctcagt aaaactgtgg tttgcaagca gaaggcgctg    1920
gaactgttgc ccaaggtgga agaggtggtg agcttaatga atgaggatga gaagactgtt    1980
gtccggctgc aggagaagcg gcagaaggag ctctggaatc tcctgaagat tgcttgtagc    2040
aaggtccgtg gtcctgtcgc tggagccccg gatgccatga atgccgctcg acttgcccag    2100
cctgggcagc tgatggctca gccgccacg gccgccaacg ccttacctga gccagccaag    2160
aaggctgaag aactggtggc tgaagcacat aacctctgca ccctgctaga aaatgccata    2220
caggacactg tgagggaaca agaccagagt ttcacggccc tagactggag ctggttacag    2280
acggaagaag aagagcacag ctgcctggag caggcctca                           2319
```

```
<210> SEQ ID NO 7
<211> LENGTH: 768
<212> TYPE: PRT
<213> ORGANISM: Artificial
<220> FEATURE:
<223> OTHER INFORMATION: IKK-alpha Inhibitory Mutant

<400> SEQUENCE: 7

His His His His Gly Asp Tyr Lys Asp Asp Asp Lys Gly Asp Ile
1               5                   10                  15

Glu Gly Arg Gly His Met Thr Met Glu Arg Pro Pro Gly Leu Arg Pro
                20                  25                  30

Gly Ala Gly Gly Pro Trp Glu Met Arg Glu Arg Leu Gly Thr Gly Gly
            35                  40                  45

Phe Gly Asn Val Cys Leu Tyr Gln His Arg Glu Leu Asp Leu Lys Ile
        50                  55                  60

Ala Ile Met Ser Cys Arg Leu Glu Leu Ser Thr Lys Asn Arg Glu Arg
65                  70                  75                  80

Trp Cys His Glu Ile Gln Ile Met Lys Lys Leu Asn His Ala Asn Val
                85                  90                  95

Val Lys Ala Cys Asp Val Pro Glu Glu Leu Asn Ile Leu Ile His Asp
            100                 105                 110

Val Pro Leu Leu Ala Met Glu Tyr Cys Ser Gly Gly Asp Leu Arg Lys
        115                 120                 125

Leu Leu Asn Lys Pro Glu Asn Cys Cys Gly Leu Lys Glu Ser Gln Ile
130                 135                 140

Leu Ser Leu Leu Ser Asp Ile Gly Ser Gly Ile Arg Tyr Leu His Glu
145                 150                 155                 160

Asn Lys Ile Ile His Arg Asp Leu Lys Pro Glu Asn Ile Val Leu Gln
                165                 170                 175

Asp Val Gly Gly Lys Ile Ile His Lys Ile Ile Asp Leu Gly Tyr Ala
            180                 185                 190

Lys Asp Val Asp Gln Gly Ser Leu Cys Thr Ser Phe Val Gly Thr Leu
        195                 200                 205

Gln Tyr Leu Ala Pro Glu Leu Phe Glu Asn Lys Pro Tyr Thr Ala Thr
210                 215                 220

Val Asp Tyr Trp Ser Phe Gly Thr Met Val Phe Glu Cys Ile Ala Gly
225                 230                 235                 240

Tyr Arg Pro Phe Leu His His Leu Gln Pro Phe Thr Trp His Glu Lys
                245                 250                 255

Ile Lys Lys Lys Asp Pro Lys Cys Ile Phe Ala Cys Glu Glu Met Ser
            260                 265                 270

Gly Glu Val Arg Phe Ser Ser His Leu Pro Gln Pro Asn Ser Leu Cys
        275                 280                 285

Ser Leu Ile Val Glu Pro Met Glu Asn Trp Leu Gln Leu Met Leu Asn
290                 295                 300

Trp Asp Pro Gln Gln Arg Gly Gly Pro Val Asp Leu Thr Leu Lys Gln
305                 310                 315                 320

Pro Arg Cys Phe Val Leu Met Asp His Ile Leu Asn Leu Lys Ile Val
                325                 330                 335

His Ile Leu Asn Met Thr Ser Ala Lys Ile Ile Ser Phe Leu Leu Pro
            340                 345                 350

Pro Asp Glu Ser Leu His Ser Leu Gln Ser Arg Ile Glu Arg Glu Thr
        355                 360                 365
```

-continued

Gly Ile Asn Thr Gly Ser Gln Glu Leu Leu Ser Glu Thr Gly Ile Ser
        370                 375                 380

Leu Asp Pro Arg Lys Pro Ala Ser Gln Cys Val Leu Asp Gly Val Arg
385                 390                 395                 400

Gly Cys Asp Ser Tyr Met Val Tyr Leu Phe Asp Lys Ser Lys Thr Val
                405                 410                 415

Tyr Glu Gly Pro Phe Ala Ser Arg Ser Leu Ser Asp Cys Val Asn Tyr
                420                 425                 430

Ile Val Gln Asp Ser Lys Ile Gln Leu Pro Ile Ile Gln Leu Arg Lys
            435                 440                 445

Ala Trp Ala Glu Ala Val His Tyr Val Ser Gly Leu Lys Glu Asp Tyr
450                 455                 460

Ser Arg Leu Phe Gln Gly Gln Arg Ala Ala Met Leu Ser Leu Leu Arg
465                 470                 475                 480

Tyr Asn Ala Asn Leu Thr Lys Met Lys Asn Thr Leu Ile Ser Ala Ser
                485                 490                 495

Gln Gln Leu Lys Ala Lys Leu Glu Phe Phe His Lys Ser Ile Gln Leu
            500                 505                 510

Asp Leu Glu Arg Tyr Ser Glu Gln Met Thr Tyr Gly Ile Ser Ser Glu
            515                 520                 525

Lys Met Leu Lys Ala Trp Lys Glu Met Glu Glu Lys Ala Ile His Tyr
530                 535                 540

Ala Glu Val Gly Val Ile Gly Tyr Leu Glu Asp Gln Ile Met Ser Leu
545                 550                 555                 560

His Ala Glu Ile Met Glu Leu Gln Lys Ser Pro Tyr Gly Arg Arg Gln
                565                 570                 575

Gly Asp Leu Met Glu Ser Leu Glu Gln Arg Ala Ile Asp Leu Tyr Lys
            580                 585                 590

Gln Leu Lys His Arg Pro Ser Asp His Ser Tyr Ser Asp Ser Thr Glu
            595                 600                 605

Met Val Lys Ile Ile Val His Thr Val Gln Ser Gln Asp Arg Val Leu
610                 615                 620

Lys Glu Leu Phe Gly His Leu Ser Lys Leu Leu Gly Cys Lys Gln Lys
625                 630                 635                 640

Ile Ile Asp Leu Leu Pro Lys Val Glu Val Ala Leu Ser Asn Ile Lys
                645                 650                 655

Glu Ala Asp Asn Thr Val Met Phe Met Gln Gly Lys Arg Gln Lys Glu
            660                 665                 670

Ile Trp His Leu Leu Lys Ile Ala Cys Thr Gln Ala Ala Ala Arg Ala
            675                 680                 685

Leu Val Gly Ala Ala Leu Glu Gly Ala Val Ala Pro Gln Ala Ala Ala
690                 695                 700

Trp Leu Pro Pro Ala Ala Ala Glu His Asp His Ala Leu Ala Cys Val
705                 710                 715                 720

Val Ala Pro Gln Asp Gly Glu Ala Ala Gln Met Ile Glu Glu Asn
                725                 730                 735

Leu Asn Cys Leu Gly His Leu Ala Ala Ile Ile His Glu Ala Asn Glu
            740                 745                 750

Glu Gln Gly Asn Ser Met Met Asn Leu Asp Trp Ser Trp Leu Thr Glu
            755                 760                 765

<210> SEQ ID NO 8
<211> LENGTH: 2238
<212> TYPE: DNA

<213> ORGANISM: Artificial
<220> FEATURE:
<223> OTHER INFORMATION: IKK-alpha Inhibitory Mutant

<400> SEQUENCE: 8

```
atggagcggc cccgggggct gcggccgggc gcgggcgggc cctgggagat gcgggagcgg        60
ctgggcaccg gcggcttcgg gaacgtctgt ctgtaccagc atcgggaact tgatctcaaa       120
atagcaatta tgtcttgtcg cctagagcta agtaccaaaa acagagaacg atggtgccat       180
gaaatccaga ttatgaagaa gttgaaccat gccaatgttg taaaggcctg tgatgttcct       240
gaagaattga atattttgat tcatgatgtg cctcttctag caatgaaata ctgttctgga       300
ggagatctcc gaaagctgct caacaaacca gaaaattgtt gtggacttaa agaaagccag       360
atactttctt tactaagtga tagggtct gggattcgat atttgcatga aaacaaaatt        420
atacatcgag atctaaaacc tgaaaacata gttcttcagg atgttggtgg aaagataata       480
cataaaataa ttgatctggg atatgccaaa gatgttgatc aaggaagtct gtgtacatct       540
tttgtgggaa cactgcagta tctggccca gagctctttg agaataagcc ttacacagcc        600
actgttgatt attggagctt tgggaccatg gtatttgaat gtattgctgg atataggcct       660
tttttgcatc atctgcagcc atttacctgg catgagaaga ttaagaagaa ggatccaaag       720
tgtatatttg catgtgaaga gatgtcacga gaagttcggt ttagtagcca tttacctcaa       780
ccaaatagcc tttgtagttt aatagtagaa cccatgaaa actggctaca gttgatgttg        840
aattgggacc ctcagcagag aggaggacct gttgaccta ctttgaagca gccaagatgt        900
tttgtattaa tggatcacat tttgaatttg aagatagtac acatcctaaa tatgacttct       960
gcaaagataa tttctttct gttaccacct gatgaaagtc ttcattcatt acagtctcgt      1020
attgagcgtg aaactggaat aaatactggt tctcaagaac ttctttcaga gacaggaatt      1080
tctctggatc ctcggaaacc agcctctcaa tgtgttctag atggagttag aggctgtgat      1140
agctatatgg tttatttgtt tgataaaagt aaaactgtat atgaagggcc atttgcttcc      1200
agaagtttat ctgattgtgt aaattatatt gtacaggaca gcaaaataca gcttccaatt      1260
atacagctgc gtaaagcgtg ggctgaagca gtgcactatg tgtctggact aaaagaagac      1320
tatagcaggc tcttttcaggg acaaagggca gcaatgttaa gtcttcttag atataatgct      1380
aacttaacaa aaatgaagaa cactttgatc tcagcatcac aacaactgaa agctaaattg      1440
gagttttttc acaaaagcat tcagcttgac ttggagagat acagcgagca gatgacgtat      1500
gggatatctt cagaaaaaat gctaaaagca tggaaagaaa tggaagaaaa ggccatccac      1560
tatgctgagg ttggtgtcat tggatacctg gaggatcaga ttatgtcttt gcatgctgaa      1620
atcatggagc tacagaagag cccctatgga agacgtcagg gagacttgat ggaatctctg      1680
gaacagcgtg ccattgatct atataagcag ttaaaacaca gaccttcaga tcactcctac      1740
agtgacagca cagagatggt gaaaatcatt gtgcacactg tgcagagtca ggaccgtgtg      1800
ctcaaggagc tgtttggtca tttgagcaag ttgttgggct gtaagcagaa gattattgat      1860
ctactcccta aggtggaagt ggccctcagt aatatcaaag aagctgacaa tactgtcatg      1920
ttcatgcagg aaaaaggca gaaagaaatc tggcatctcc ttaaaattgc ctgtacacag      1980
gccgctgccc gcgcccttgt gggagccgct ctggaaggtg cagtggcccc acaggccgcc      2040
gcatggctgc cccctgctgc cgcagaacac gatcacgctc tggcctgtgt ggtggctcct      2100
caagatgggg aggctgccgc acaaatgatc gaagaaaatt tgaactgcct tggccacttg      2160
gccgctatta ttcacgaggc aaatgaggaa cagggcaata gtatgatgaa tcttgattgg      2220
```
agttggttga cagaatga 2238

<210> SEQ ID NO 9
<211> LENGTH: 779
<212> TYPE: PRT
<213> ORGANISM: Artificial
<220> FEATURE:
<223> OTHER INFORMATION: IKK-beta Inhibitory Mutant

<400> SEQUENCE: 9

Ser His His His His His Gly Asp Tyr Lys Asp Asp Asp Lys Gly
1               5                   10                  15

Asp Ile Glu Gly Arg Gly His Met Ser Trp Ser Pro Ser Leu Thr Thr
            20                  25                  30

Gln Thr Cys Gly Ala Trp Glu Met Lys Glu Arg Leu Gly Thr Gly Gly
        35                  40                  45

Phe Gly Asn Val Ile Arg Trp His Asn Gln Glu Thr Gly Glu Gln Ile
    50                  55                  60

Ala Ile Met Gln Cys Arg Gln Glu Leu Ser Pro Arg Asn Arg Glu Arg
65                  70                  75                  80

Trp Cys Leu Glu Ile Gln Ile Met Arg Arg Leu Thr His Pro Asn Val
                85                  90                  95

Val Ala Ala Arg Asp Val Pro Glu Gly Met Gln Asn Leu Ala Pro Asn
            100                 105                 110

Asp Leu Pro Leu Leu Ala Met Glu Tyr Cys Gln Gly Gly Asp Leu Arg
        115                 120                 125

Lys Tyr Leu Asn Gln Phe Glu Asn Cys Cys Gly Leu Arg Glu Gly Ala
    130                 135                 140

Ile Leu Thr Leu Leu Ser Asp Ile Ala Ser Ala Leu Arg Tyr Leu His
145                 150                 155                 160

Glu Asn Arg Ile Ile His Arg Asp Leu Lys Pro Glu Asn Ile Val Leu
                165                 170                 175

Gln Gln Gly Glu Gln Arg Leu Ile His Lys Ile Ile Asp Leu Gly Tyr
            180                 185                 190

Ala Lys Glu Leu Asp Gln Gly Ser Leu Cys Thr Ser Phe Val Gly Thr
        195                 200                 205

Leu Gln Tyr Leu Ala Pro Glu Leu Leu Glu Gln Gln Lys Tyr Thr Val
    210                 215                 220

Thr Val Asp Tyr Trp Ser Phe Gly Thr Leu Ala Phe Glu Cys Ile Thr
225                 230                 235                 240

Gly Phe Arg Pro Phe Leu Pro Asn Trp Gln Pro Val Gln Trp His Ser
                245                 250                 255

Lys Val Arg Gln Lys Ser Glu Val Asp Ile Val Val Ser Glu Asp Leu
            260                 265                 270

Asn Gly Thr Val Lys Phe Ser Ser Leu Pro Tyr Pro Asn Asn Leu
        275                 280                 285

Asn Ser Val Leu Ala Glu Arg Leu Glu Lys Trp Leu Gln Leu Met Leu
    290                 295                 300

Met Trp His Pro Arg Gln Arg Gly Thr Asp Pro Thr Tyr Gly Pro Asn
305                 310                 315                 320

Gly Cys Phe Lys Ala Leu Asp Asp Ile Leu Asn Leu Lys Leu Val His
                325                 330                 335

Ile Leu Asn Met Val Thr Gly Thr Ile His Thr Tyr Pro Val Thr Glu
            340                 345                 350

```
Asp Glu Ser Leu Gln Ser Leu Lys Ala Arg Ile Gln Gln Asp Thr Gly
            355                 360                 365
Ile Pro Glu Glu Asp Gln Glu Leu Leu Gln Glu Ala Gly Leu Ala Leu
    370                 375                 380
Ile Pro Asp Lys Pro Ala Thr Gln Cys Ile Ser Asp Gly Lys Leu Asn
385                 390                 395                 400
Glu Gly His Thr Leu Asp Met Asp Leu Val Phe Leu Phe Asp Asn Ser
                405                 410                 415
Lys Ile Thr Tyr Glu Thr Gln Ile Ser Pro Arg Pro Gln Pro Glu Ser
            420                 425                 430
Val Ser Cys Ile Leu Gln Glu Pro Lys Arg Asn Leu Ala Phe Phe Gln
    435                 440                 445
Leu Arg Lys Val Trp Gly Gln Val Trp His Ser Ile Gln Thr Leu Lys
    450                 455                 460
Glu Asp Cys Asn Arg Leu Gln Gln Gly Gln Arg Ala Ala Met Met Asn
465                 470                 475                 480
Leu Leu Arg Asn Asn Ser Cys Leu Ser Lys Met Lys Asn Ser Met Ala
                485                 490                 495
Ser Met Ser Gln Gln Leu Lys Ala Lys Leu Asp Phe Phe Lys Thr Ser
            500                 505                 510
Ile Gln Ile Asp Leu Glu Lys Tyr Ser Glu Gln Thr Glu Phe Gly Ile
    515                 520                 525
Thr Ser Asp Lys Leu Leu Leu Ala Trp Arg Glu Met Glu Gln Ala Val
    530                 535                 540
Glu Leu Cys Gly Arg Glu Asn Glu Val Lys Leu Leu Val Glu Arg Met
545                 550                 555                 560
Met Ala Leu Gln Thr Asp Ile Val Asp Leu Gln Arg Ser Pro Met Gly
                565                 570                 575
Arg Lys Gln Gly Gly Thr Leu Asp Asp Leu Glu Glu Gln Ala Arg Glu
            580                 585                 590
Leu Tyr Arg Arg Leu Arg Glu Lys Pro Arg Asp Gln Arg Thr Glu Gly
    595                 600                 605
Asp Ser Gln Glu Met Val Arg Leu Leu Leu Gln Ala Ile Gln Ser Phe
    610                 615                 620
Glu Lys Lys Val Arg Val Ile Tyr Thr Gln Leu Ser Lys Thr Val Val
625                 630                 635                 640
Cys Lys Gln Lys Ala Leu Glu Leu Leu Pro Lys Val Glu Glu Val Val
                645                 650                 655
Ser Leu Met Asn Glu Asp Glu Lys Thr Val Val Arg Leu Gln Glu Lys
            660                 665                 670
Arg Gln Lys Glu Leu Trp Asn Leu Leu Lys Ile Ala Cys Ser Lys Val
    675                 680                 685
Arg Gly Pro Val Ala Gly Ala Pro Asp Ala Met Asn Ala Ala Arg Leu
    690                 695                 700
Ala Gln Pro Gly Gln Leu Met Ala Gln Pro Ala Thr Ala Ala Asn Ala
705                 710                 715                 720
Leu Pro Glu Pro Ala Lys Lys Ala Glu Glu Leu Val Ala Glu Ala His
                725                 730                 735
Asn Leu Cys Thr Leu Leu Glu Asn Ala Ile Gln Asp Thr Val Arg Glu
            740                 745                 750
Gln Asp Gln Ser Phe Thr Ala Leu Asp Trp Ser Trp Leu Gln Thr Glu
    755                 760                 765
Glu Glu Glu His Ser Cys Leu Glu Gln Ala Ser
```

```
                770                 775
```

<210> SEQ ID NO 10
<211> LENGTH: 2271
<212> TYPE: PRT
<213> ORGANISM: Artificial
<220> FEATURE:
<223> OTHER INFORMATION: IKK-beta Inhibitory Mutant

<400> SEQUENCE: 10

Ala Thr Gly Ala Gly Cys Thr Gly Gly Thr Cys Ala Cys Cys Thr Thr
1 5 10 15

Cys Cys Cys Thr Gly Ala Cys Ala Ala Cys Gly Cys Ala Gly Ala Cys
20 25 30

Ala Thr Gly Cys Gly Gly Gly Gly Cys Cys Thr Gly Gly Gly Ala Ala
35 40 45

Ala Thr Gly Ala Ala Ala Gly Ala Gly Cys Gly Cys Cys Thr Thr Gly
50 55 60

Gly Gly Ala Cys Ala Gly Gly Gly Gly Gly Ala Thr Thr Thr Gly Gly
65 70 75 80

Ala Ala Ala Thr Gly Thr Cys Ala Thr Cys Cys Gly Ala Thr Gly Gly
85 90 95

Cys Ala Cys Ala Ala Thr Cys Ala Gly Gly Ala Ala Ala Cys Ala Gly
100 105 110

Gly Thr Gly Ala Gly Cys Ala Gly Ala Thr Thr Gly Cys Cys Ala Thr
115 120 125

Cys Ala Thr Gly Cys Ala Gly Thr Gly Cys Cys Gly Gly Cys Ala Gly
130 135 140

Gly Ala Gly Cys Thr Cys Ala Gly Cys Cys Cys Cys Cys Gly Gly Ala
145 150 155 160

Ala Cys Cys Gly Ala Gly Ala Gly Cys Gly Gly Thr Gly Gly Thr Gly
165 170 175

Cys Cys Thr Gly Gly Ala Gly Ala Thr Cys Cys Ala Gly Ala Thr Cys
180 185 190

Ala Thr Gly Ala Gly Ala Ala Gly Gly Cys Thr Gly Ala Cys Cys Cys
195 200 205

Ala Cys Cys Cys Cys Ala Ala Thr Gly Thr Gly Gly Thr Gly Gly Cys
210 215 220

Thr Gly Cys Cys Cys Gly Ala Gly Ala Thr Gly Thr Cys Cys Cys Thr
225 230 235 240

Gly Ala Gly Gly Gly Gly Ala Thr Gly Cys Ala Gly Ala Ala Cys Thr
245 250 255

Thr Gly Gly Cys Gly Cys Cys Cys Ala Ala Thr Gly Ala Cys Cys Thr
260 265 270

Gly Cys Cys Cys Cys Thr Gly Cys Thr Gly Gly Cys Cys Ala Thr Gly
275 280 285

Gly Ala Gly Thr Ala Cys Thr Gly Cys Cys Ala Ala Gly Gly Ala Gly
290 295 300

Gly Ala Gly Ala Thr Cys Thr Cys Cys Gly Gly Ala Ala Gly Thr Ala
305 310 315 320

Cys Cys Thr Gly Ala Ala Cys Cys Ala Gly Thr Thr Thr Gly Ala Gly
325 330 335

Ala Ala Cys Thr Gly Cys Thr Gly Thr Gly Gly Thr Cys Thr Gly Cys
340 345 350

Gly Gly Gly Ala Ala Gly Gly Thr Gly Cys Cys Ala Thr Cys Cys Thr

```
                    355                 360                 365
Cys Ala Cys Cys Thr Thr Gly Cys Thr Gly Ala Gly Thr Gly Ala Cys
            370                 375                 380

Ala Thr Thr Gly Cys Cys Thr Cys Thr Gly Cys Gly Cys Thr Thr Ala
385                 390                 395                 400

Gly Ala Thr Ala Cys Cys Thr Thr Cys Ala Thr Gly Ala Ala Ala Ala
                        405                 410                 415

Cys Ala Gly Ala Ala Thr Cys Ala Thr Cys Cys Ala Thr Cys Gly Gly
                420                 425                 430

Gly Ala Thr Cys Thr Ala Ala Ala Gly Cys Cys Ala Gly Ala Ala Ala
                435                 440                 445

Ala Cys Ala Thr Cys Gly Thr Cys Cys Thr Gly Cys Ala Gly Cys Ala
            450                 455                 460

Ala Gly Gly Ala Gly Ala Ala Cys Ala Gly Ala Gly Gly Thr Thr Ala
465                 470                 475                 480

Ala Thr Ala Cys Ala Cys Ala Ala Ala Thr Thr Ala Thr Thr Thr Gly
                485                 490                 495

Ala Cys Cys Thr Ala Gly Gly Ala Thr Ala Thr Gly Cys Cys Ala Ala
            500                 505                 510

Gly Gly Ala Gly Cys Thr Gly Gly Ala Thr Cys Ala Gly Gly Gly Cys
        515                 520                 525

Ala Gly Thr Cys Thr Thr Thr Gly Cys Ala Cys Ala Thr Cys Ala Thr
        530                 535                 540

Thr Cys Gly Thr Gly Gly Gly Ala Cys Cys Thr Gly Cys Ala
545                 550                 555                 560

Gly Thr Ala Cys Cys Thr Gly Gly Cys Cys Cys Ala Gly Ala Gly
            565                 570                 575

Cys Thr Ala Cys Thr Gly Gly Ala Gly Cys Ala Gly Cys Ala Gly Ala
            580                 585                 590

Ala Gly Thr Ala Cys Ala Cys Ala Gly Thr Gly Ala Cys Cys Gly Thr
        595                 600                 605

Cys Gly Ala Cys Thr Ala Cys Thr Gly Gly Ala Gly Cys Thr Thr Cys
    610                 615                 620

Gly Gly Cys Ala Cys Cys Cys Thr Gly Gly Cys Cys Thr Thr Thr Gly
625                 630                 635                 640

Ala Gly Thr Gly Cys Ala Thr Cys Ala Cys Gly Gly Gly Cys Thr Thr
            645                 650                 655

Cys Cys Gly Gly Cys Cys Cys Thr Thr Cys Cys Thr Cys Cys Cys
            660                 665                 670

Ala Ala Cys Thr Gly Gly Cys Ala Gly Cys Cys Gly Thr Gly Cys
        675                 680                 685

Ala Gly Thr Gly Gly Cys Ala Thr Thr Cys Ala Ala Ala Gly Thr
        690                 695                 700

Gly Cys Gly Gly Cys Ala Gly Ala Ala Gly Ala Gly Thr Gly Ala Gly
705                 710                 715                 720

Gly Thr Gly Gly Ala Cys Ala Thr Thr Gly Thr Gly Thr Thr Ala
                725                 730                 735

Gly Cys Gly Ala Ala Gly Ala Cys Thr Thr Gly Ala Ala Thr Gly Gly
            740                 745                 750

Ala Ala Cys Gly Gly Thr Gly Ala Ala Gly Thr Thr Thr Thr Cys Ala
            755                 760                 765

Ala Gly Cys Thr Cys Thr Thr Thr Ala Cys Cys Cys Thr Ala Cys Cys
        770                 775                 780
```

-continued

Cys Cys Ala Ala Thr Ala Ala Thr Cys Thr Thr Ala Ala Cys Ala Gly
785 790 795 800

Thr Gly Thr Cys Cys Thr Gly Gly Cys Thr Gly Ala Gly Cys Gly Ala
805 810 815

Cys Thr Gly Gly Ala Gly Ala Ala Gly Thr Gly Gly Cys Thr Gly Cys
820 825 830

Ala Ala Cys Thr Gly Ala Thr Gly Cys Thr Gly Ala Thr Gly Thr Gly
835 840 845

Gly Cys Ala Cys Cys Cys Cys Cys Gly Ala Cys Ala Gly Ala Gly Gly
850 855 860

Gly Gly Cys Ala Cys Gly Gly Ala Thr Cys Cys Cys Ala Cys Gly Thr
865 870 875 880

Ala Thr Gly Gly Gly Cys Cys Cys Ala Ala Thr Gly Gly Cys Thr Gly
885 890 895

Cys Thr Thr Cys Ala Ala Gly Gly Cys Cys Cys Thr Gly Gly Ala Thr
900 905 910

Gly Ala Cys Ala Thr Cys Thr Thr Ala Ala Ala Cys Thr Thr Ala Ala
915 920 925

Ala Gly Cys Thr Gly Gly Thr Thr Cys Ala Thr Ala Thr Cys Thr Thr
930 935 940

Gly Ala Ala Cys Ala Thr Gly Gly Thr Cys Ala Cys Gly Gly Gly Cys
945 950 955 960

Ala Cys Cys Ala Thr Cys Cys Ala Cys Ala Cys Cys Thr Ala Cys Cys
965 970 975

Cys Thr Gly Thr Gly Ala Cys Ala Gly Ala Gly Gly Ala Thr Gly Ala
980 985 990

Gly Ala Gly Thr Cys Thr Gly Cys Ala Gly Ala Gly Cys Thr Thr Gly
995 1000 1005

Ala Ala Gly Gly Cys Cys Ala Gly Ala Ala Thr Cys Cys Ala Ala
1010 1015 1020

Cys Ala Gly Gly Ala Cys Ala Cys Gly Gly Gly Cys Ala Thr Cys
1025 1030 1035

Cys Cys Ala Gly Ala Gly Gly Ala Gly Gly Ala Cys Cys Ala Gly
1040 1045 1050

Gly Ala Gly Cys Thr Gly Cys Thr Gly Cys Ala Gly Gly Ala Ala
1055 1060 1065

Gly Cys Gly Gly Gly Cys Cys Thr Gly Gly Cys Gly Thr Thr Gly
1070 1075 1080

Ala Thr Cys Cys Cys Cys Gly Ala Thr Ala Ala Gly Cys Cys Thr
1085 1090 1095

Gly Cys Cys Ala Cys Thr Cys Ala Gly Thr Gly Thr Ala Thr Thr
1100 1105 1110

Thr Cys Ala Gly Ala Cys Gly Gly Cys Ala Ala Gly Thr Thr Ala
1115 1120 1125

Ala Ala Thr Gly Ala Gly Gly Gly Cys Cys Ala Cys Ala Cys Ala
1130 1135 1140

Thr Thr Gly Gly Ala Cys Ala Thr Gly Gly Ala Thr Cys Thr Thr
1145 1150 1155

Gly Thr Thr Thr Thr Thr Cys Thr Cys Thr Thr Thr Gly Ala Cys
1160 1165 1170

Ala Ala Cys Ala Gly Thr Ala Ala Ala Ala Thr Cys Ala Cys Cys
1175 1180 1185

```
Thr Ala Thr Gly Ala Gly Ala Cys Thr Cys Ala Gly Ala Thr Cys
1190            1195                1200

Thr Cys Cys Cys Cys Ala Cys Gly Gly Cys Cys Cys Cys Ala Ala
1205            1210                1215

Cys Cys Thr Gly Ala Ala Ala Gly Thr Gly Thr Cys Ala Gly Cys
1220            1225                1230

Thr Gly Thr Ala Thr Cys Cys Thr Thr Cys Ala Ala Gly Ala Gly
1235            1240                1245

Cys Cys Cys Ala Ala Gly Ala Gly Gly Ala Ala Thr Cys Thr Cys
1250            1255                1260

Gly Cys Cys Thr Thr Cys Thr Thr Cys Cys Ala Gly Cys Thr Gly
1265            1270                1275

Ala Gly Gly Ala Ala Gly Gly Thr Gly Thr Gly Gly Gly Gly Cys
1280            1285                1290

Cys Ala Gly Gly Thr Cys Thr Gly Gly Cys Ala Cys Ala Gly Cys
1295            1300                1305

Ala Thr Cys Cys Ala Gly Ala Cys Cys Cys Thr Gly Ala Ala Gly
1310            1315                1320

Gly Ala Ala Gly Ala Thr Thr Gly Cys Ala Ala Cys Cys Gly Gly
1325            1330                1335

Cys Thr Gly Cys Ala Gly Cys Ala Gly Gly Ala Cys Ala Gly Cys
1340            1345                1350

Cys Gly Ala Gly Cys Cys Gly Cys Cys Ala Thr Gly Ala Thr Gly
1355            1360                1365

Ala Ala Thr Cys Thr Cys Cys Thr Cys Cys Gly Ala Ala Ala Cys
1370            1375                1380

Ala Ala Cys Ala Gly Cys Thr Gly Cys Cys Thr Cys Thr Cys Cys
1385            1390                1395

Ala Ala Ala Ala Thr Gly Ala Ala Gly Ala Ala Thr Thr Cys Cys
1400            1405                1410

Ala Thr Gly Gly Cys Thr Thr Cys Cys Ala Thr Gly Thr Cys Thr
1415            1420                1425

Cys Ala Gly Cys Ala Gly Cys Thr Cys Ala Ala Gly Gly Cys Cys
1430            1435                1440

Ala Ala Gly Thr Thr Gly Gly Ala Thr Thr Thr Cys Thr Thr Cys
1445            1450                1455

Ala Ala Ala Ala Cys Cys Ala Gly Cys Ala Thr Cys Cys Ala Gly
1460            1465                1470

Ala Thr Thr Gly Ala Cys Cys Thr Gly Gly Ala Gly Ala Ala Gly
1475            1480                1485

Thr Ala Cys Ala Gly Cys Gly Ala Gly Cys Ala Ala Ala Cys Cys
1490            1495                1500

Gly Ala Gly Thr Thr Thr Gly Gly Gly Ala Thr Cys Ala Cys Ala
1505            1510                1515

Thr Cys Ala Gly Ala Thr Ala Ala Ala Cys Thr Gly Cys Thr Gly
1520            1525                1530

Cys Thr Gly Gly Cys Cys Thr Gly Gly Ala Gly Gly Gly Ala Ala
1535            1540                1545

Ala Thr Gly Gly Ala Gly Cys Ala Gly Cys Thr Gly Thr Gly Gly
1550            1555                1560

Gly Ala Gly Cys Thr Cys Thr Gly Thr Gly Gly Cys Gly Gly
1565            1570                1575

Gly Ala Gly Ala Ala Cys Gly Ala Ala Gly Thr Gly Ala Ala Ala
```

-continued

```
            1580                1585                1590

Cys Thr Cys Cys Thr Gly Gly Thr Ala Gly Ala Ala Cys Gly Gly
    1595                1600                1605

Ala Thr Gly Ala Thr Gly Gly Cys Thr Cys Thr Gly Cys Ala Gly
    1610                1615                1620

Ala Cys Cys Gly Ala Cys Ala Thr Thr Gly Thr Gly Gly Ala Cys
    1625                1630                1635

Thr Thr Ala Cys Ala Gly Ala Gly Gly Ala Gly Cys Cys Cys Cys
    1640                1645                1650

Ala Thr Gly Gly Gly Cys Cys Gly Gly Ala Ala Gly Cys Ala Gly
    1655                1660                1665

Gly Gly Gly Gly Gly Ala Ala Cys Gly Cys Thr Gly Gly Ala Cys
    1670                1675                1680

Gly Ala Cys Cys Thr Ala Gly Ala Gly Gly Ala Gly Cys Ala Ala
    1685                1690                1695

Gly Cys Ala Ala Gly Gly Ala Gly Cys Thr Gly Thr Ala Cys
    1700                1705                1710

Ala Gly Gly Ala Gly Ala Cys Thr Ala Ala Gly Gly Ala Ala
    1715                1720                1725

Ala Ala Ala Cys Cys Thr Cys Gly Ala Gly Ala Cys Cys Ala Gly
    1730                1735                1740

Cys Gly Ala Ala Cys Thr Gly Ala Gly Gly Gly Thr Gly Ala Cys
    1745                1750                1755

Ala Gly Thr Cys Ala Gly Gly Ala Ala Ala Thr Gly Gly Thr Ala
    1760                1765                1770

Cys Gly Gly Cys Thr Gly Cys Thr Gly Cys Thr Thr Cys Ala Gly
    1775                1780                1785

Gly Cys Ala Ala Thr Thr Cys Ala Gly Ala Gly Cys Thr Thr Cys
    1790                1795                1800

Gly Ala Gly Ala Ala Gly Ala Ala Ala Gly Thr Gly Cys Gly Ala
    1805                1810                1815

Gly Thr Gly Ala Thr Cys Thr Ala Thr Ala Cys Gly Cys Ala Gly
    1820                1825                1830

Cys Thr Cys Ala Gly Thr Ala Ala Ala Cys Thr Gly Thr Gly
    1835                1840                1845

Gly Thr Thr Thr Gly Cys Ala Ala Gly Cys Ala Gly Ala Ala Gly
    1850                1855                1860

Gly Cys Gly Cys Thr Gly Gly Ala Ala Cys Thr Gly Thr Thr Gly
    1865                1870                1875

Cys Cys Cys Ala Ala Gly Gly Thr Gly Gly Ala Ala Gly Ala Gly
    1880                1885                1890

Gly Thr Gly Gly Thr Gly Ala Gly Cys Thr Thr Ala Ala Thr Gly
    1895                1900                1905

Ala Ala Thr Gly Ala Gly Gly Ala Thr Gly Ala Gly Ala Ala Gly
    1910                1915                1920

Ala Cys Thr Gly Thr Thr Gly Thr Cys Cys Gly Gly Cys Thr Gly
    1925                1930                1935

Cys Ala Gly Gly Ala Gly Ala Ala Gly Cys Gly Gly Cys Ala Gly
    1940                1945                1950

Ala Ala Gly Gly Ala Gly Cys Thr Cys Thr Gly Gly Ala Ala Thr
    1955                1960                1965

Cys Thr Cys Cys Thr Gly Ala Ala Gly Ala Thr Thr Gly Cys Thr
    1970                1975                1980
```

-continued

```
Thr Gly  Thr Ala Gly Cys Ala  Ala Gly Gly Thr Cys  Cys Gly Thr
    1985                 1990                 1995

Gly Gly  Thr Cys Cys Thr Gly  Thr Cys Gly Cys Thr  Gly Gly Ala
    2000                 2005                 2010

Gly Cys  Cys Cys Cys Gly Gly  Ala Thr Gly Cys Cys  Ala Thr Gly
    2015                 2020                 2025

Ala Ala  Thr Gly Cys Cys Gly  Cys Thr Cys Gly Ala  Cys Thr Thr
    2030                 2035                 2040

Gly Cys  Cys Cys Ala Gly Cys  Cys Thr Gly Gly Gly  Cys Ala Gly
    2045                 2050                 2055

Cys Thr  Gly Ala Thr Gly Gly  Cys Thr Cys Ala Gly  Cys Cys Cys
    2060                 2065                 2070

Gly Cys  Cys Ala Cys Gly Gly  Cys Cys Gly Cys Cys  Ala Ala Cys
    2075                 2080                 2085

Gly Cys  Cys Thr Thr Ala Cys  Cys Thr Gly Ala Gly  Cys Cys Ala
    2090                 2095                 2100

Gly Cys  Cys Ala Ala Gly Ala  Ala Gly Gly Cys Thr  Gly Ala Ala
    2105                 2110                 2115

Gly Ala  Ala Cys Thr Gly Gly  Thr Gly Gly Cys Thr  Gly Ala Ala
    2120                 2125                 2130

Gly Cys  Ala Cys Ala Thr Ala  Ala Cys Cys Thr Cys  Thr Gly Cys
    2135                 2140                 2145

Ala Cys  Cys Cys Thr Gly Cys  Thr Ala Gly Ala Ala  Ala Ala Thr
    2150                 2155                 2160

Gly Cys  Cys Ala Thr Ala Cys  Ala Gly Gly Ala Cys  Ala Cys Thr
    2165                 2170                 2175

Gly Thr  Gly Ala Gly Gly Gly  Ala Ala Cys Ala Ala  Gly Ala Cys
    2180                 2185                 2190

Cys Ala  Gly Ala Gly Thr Thr  Thr Cys Ala Cys Gly  Gly Cys Cys
    2195                 2200                 2205

Cys Thr  Ala Gly Ala Cys Thr  Gly Gly Ala Gly Cys  Thr Gly Gly
    2210                 2215                 2220

Thr Thr  Ala Cys Ala Gly Ala  Cys Gly Gly Ala Ala  Gly Ala Ala
    2225                 2230                 2235

Gly Ala  Ala Gly Ala Gly Cys  Ala Cys Ala Gly Cys  Thr Gly Cys
    2240                 2245                 2250

Cys Thr  Gly Gly Ala Gly Cys  Ala Gly Gly Cys Cys  Thr Cys Ala
    2255                 2260                 2265

Thr Gly  Ala
    2270
```

NF-KB SIGNALING PATHWAY-MANIPULATED DENDRITIC CELLS

RELATED APPLICATIONS

This application is a divisional of U.S. patent application Ser. No. 13/881,592, filed on Sep. 9, 2013, which is a U.S. National Stage Application under 35 U.S.C. § 371 of International Application No. PCT/EP2011/005400, filed on Oct. 26, 2011, which claims priority to European Patent Application No. 10188893.1, filed on Oct. 26, 2010, the contents of which applications are incorporated by reference herein in their entirety.

SEQUENCE LISTING

The text file entitled "T3091_PCT_sequence_listing.txt," created on Aug. 11, 2017, having 68 kilobytes of data, and filed concurrently herewith, is hereby incorporated by reference in its entirety in this application.

FIELD OF THE INVENTION

The invention relates to dendritic cells, the NFκB signaling pathway of which has been manipulated by RNA transfection, to the manufacture thereof and to use thereof.

BACKGROUND OF THE INVENTION

In the specification, reference is made to a number of documents from the prior art including patent applications and manufacturer's manuals. While the disclosure of these documents is not considered relevant to the patentability of the invention, it is incorporated by reference into the present specification.

Dendritic cells (DCs) are the link between the innate and the adaptive immune response. They are able to detect pathogens as such, and to initialize and direct an adaptive (that is, tailored to the specific pathogen) immune response. In the absence of pathogens, DCs are also capable of mediating tolerance against endogenous antigens. Thus, DCs are the key for the targeted induction of immune responses, but also for mediating immunological tolerance. The cytokine IL-12p70 plays an important role in the induction of cell mediated immunity, while the cytokine IL-10 is involved in the induction of humoral immunity, and also of tolerance. Immunotherapy of malignant diseases using DCs as adjuvants was tested already in various clinical trials, where the safety and feasibility of this method could be demonstrated. However, the clinical outcomes remained below expectations, although frequently the patients' immune responses against the antigens used were detectable in vitro. Generating the DCs in cell culture offers the opportunity to manipulate them in a targeted way. For this purpose, it is advantageous to generate DCs, which are able to induce long-lived memory T cells, and thereby act resistant to regulatory T cells (Tregs) and other tolerogenic mechanisms. Upon re-exposure to an antigen, long-lived memory T cells can mediate a more rapid and more efficient secondary response. This memory function can be provided by $CD4^+$ and $CD8^+$ memory T cells. Long-lived memory T cells are different from effector cells that only have a short life time and usually die after an immune response by activation-inducing cell death (AICD). Between the two cell types, however, there are transitional forms, such as the effector memory cells. Like effector cells, they are able to patrol throughout the body, and exert an effector function upon antigen contact, and they can proliferate and are also more long-lived than effector cells. On the other hand, the use of DCs for the targeted treatment of autoimmunity and allergies is conceivable because DCs can suppress immune responses and mediate tolerance under certain conditions. Improved methods and protocols for the manufacture of various types of DCs are therefore of great interest and are the object of research worldwide. An overview of the current prior art is presented in Boczkowski and Nair, Expert Opin. Biol. Ther. 10 (4) (2010), 563-574, and in Kaisho and Tanaka, Trends in Immunology 29 (7) (2008), 329-336.

DCs have a variety of surface receptors with which they can identify various pathogens. In addition, DCs are able to perceive various endogenous messengers such as cytokines and chemokines, and surface molecules on other cells of the immune system. The DC processes the various incoming signals via intracellular signaling pathways, whereby various differentiation programs are triggered. The targeted manipulation of these signaling pathways may allow the creation of tailor-made DCs, which are thus better suited to mediate either immunity (in cancer immunotherapy) or tolerance (in the treatment of autoimmune diseases and allergies).

Different ways to intervene in the signaling pathways in the DC through genetic manipulation have already been formulated and implemented. However, various barriers get in the way, especially in the manipulation of human DCs. Genetic manipulation in the context of a therapy gives cause for concern, and somatic gene therapy is tightly regulated. In addition, the options of genetically modifying the human DCs most widely used in medicine (monocyte-derived DCs) are very limited, and only the use of viral transfection systems, which were developed from lentiviruses or adenoviruses, has been successful so far. The use of such vehicles for introducing DNA, however, has been viewed very critically, and bears additional risks. For example, by using lentiviruses, viral sequences are also always incorporated into the genome of the cell. This may destroy active endogenous genes, or the viral promoters may activate genes that would otherwise be inactive. Since integration into the genome is random, however, it is impossible to predict which genes may be affected. If tumor suppressor genes or oncogenes are destroyed or activated, the cell, in the worst case, may become a tumor cell. Also, the induced immune response may be directed against the viral products rather than against the desired antigens. The latter also applies to adenoviral systems, where, in this case, the immune response may be very severe, since many people already have an existing immune response against adenoviruses. In 1999, such a severe immune response against an adenoviral vector even resulted in a fatality.

A central signaling pathway of the DC is the NFκB signaling cascade. Stimulation of many of the surface receptors of the DC leads to activation of this cascade, wherein inhibitory proteins are destabilized by phosphorylation, so that transcription factors will enter the nucleus where they cause the transcription of various genes. The kinases that perform such phosphorylation are called IKK (inhibitor of kappa kinases).

SUMMARY OF THE INVENTION

It has now been found that dendritic cells (hereinafter referred to as "DCs") can be manipulated in their NFκB signaling pathway by RNA transfection and expression of mutant signal-transducing proteins of the NFκB signaling pathway. Both constitutively active and dominant negative mutants were found. By the maturation of the DC prior to or after the RNA transfection, DCs with various phenotypes and cytokine profiles may be produced, with cytokines IL-12p70 (for induction of immunity) and IL-10 (for induction of tolerance or for generating immunosuppressed phenotypes) playing central roles. Thus, the invention relates to:

(1) Dendritic cells (DCs), the NFκB signaling pathway of which has been manipulated by RNA transfection with one or more nucleotide sequences encoding at least one mutant signal transducing protein of the NFκB signaling pathway;
(2) a method for the manufacture of NFκB signaling pathway manipulated DCs according to (1), comprising the RNA transfection of immature or mature DCs with one or more nucleotide sequences encoding a mutant signal transducing protein of the NFκB signaling pathway;
(3) a composition, pharmaceutical composition or drug comprising DCs according to (1);
(4) the use of the DC according to (1) for the stimulation of autologous CD8+ T cells ex vivo;
(5) the use according to (1) for manufacturing a drug for the treatment and prevention of cancer and infectious diseases, such as HIV-mediated AIDS or autoimmune diseases in a patient; and to the same extent the DCs according to (1) for the treatment and prevention of cancer and infectious diseases or autoimmune diseases in a patient
(6) a process for the expansion of T cells, including the stimulation of autologous CD8+ T cells ex vivo, comprising stimulating the cells with DCs according to (1); and
(7) a method for the treatment of cancer, infectious diseases or autoimmune diseases in a patient, comprising administering the DCs according to (1) to said patient.

BRIEF DESCRIPTION OF THE FIGURES

FIG. 6: Induction factor of surface markers on DCs, which were electroporated with components of the NFκB signaling pathway. DCs were produced from monocytes during a six-day culture with GM-CSF and IL-4. On Day 6, the DCs matured for 24 h after addition of a standard maturation cocktail (IL-1β, IL-6, TNFα and PGE2) (mDC). Then, the DCs were electroporated without RNA, with IKKα-EE-A16-RNA (activates alternative signaling pathway), IKKβ-EEA10-RNA (activates classical signaling pathway) alone or in combination (15 μg of RNA each). These DCs were stained 24 h after EP with antibodies against CD 40 and CD70, and analyzed by FACS. The mean of 8 independent donors is provided with the standard error of the mean.

FIG. 7: Induction factor of surface markers on DCs, which were electroporated with components of the NFκB signaling pathway. DCs were produced from monocytes during a six-day culture with GM-CSF and IL-4. On Day 6, the DCs matured for 24 h after addition of a standard maturation cocktail (IL-1β, IL-6, TNFα and PGE2) (mDC). Then, the DCs were electroporated without RNA, with IKKα-EE-A16-RNA (activates alternative signaling pathway), IKKβ-EEA10-RNA (activates classical signaling pathway) alone or in combination (15 μg of RNA each). These DCs were stained 24 h after EP with antibodies against CD83 and CD86, and analyzed by FACS. The mean of 8 independent donors is provided with the standard error of the mean.

FIG. 8: Induction factor of surface markers on DCs, which were electroporated with components of the NFκB signaling pathway. DCs were produced from monocytes during a six-day culture with GM-CSF and IL-4. On Day 6, the DCs matured for 24 h after addition of a standard maturation cocktail (IL-1β, IL-6, TNFα and PGE2) (mDC). Then, the DCs were electroporated without RNA, with IKKα-EE-A16-RNA (activates alternative signaling pathway), IKKβ-EEA10-RNA (activates classical signaling pathway) alone or in combination (15 μg of RNA each). These DCs were stained 24 h after EP with antibodies against OX-40L and CD25, and analyzed by FACS. The mean of 8 independent donors is provided with the standard error of the mean.

FIG. 9: Secretion of cytokines IL-12p70 and IL-10 by DCs, which were electroporated with components of the NFκB signaling pathway. DCs were produced from monocytes during a six-day culture with GM-CSF and IL-4. On Day 6, the DCs matured for 24 h after addition of a standard maturation cocktail (IL-1β, IL-6, TNFα and PGE2) (mDC). Then, the DCs were electroporated without RNA, with IKKα-EE-A16-RNA (activates alternative signaling pathway), IKKβ-EEA10-RNA (activates classical signaling pathway) alone or in combination (15 μg of RNA each). 24 h after EP, the supernatants were collected and analyzed by an "inflammation cytometric bead array". The data from 3 independent donors are shown.

FIG. 10: Secretion of cytokines IL-6 and TNFα by DCs, which were electroporated with components of the NFκB signaling pathway. DCs were produced from monocytes during a six-day culture with GM-CSF and IL-4. On Day 6, the DCs matured for 24 h after addition of a standard maturation cocktail (IL-1β, IL-6, TNFα and PGE2) (mDC). Then, the DCs were electroporated without RNA, with IKKα-EE-A16-RNA (activates alternative signaling pathway), IKKβ-EEA10-RNA (activates classical signaling pathway) alone or in combination (15 μg of RNA each). 24 h after EP, the supernatants were collected and analyzed by an "inflammation cytometric bead array". The data from 3 independent donors are shown.

FIG. 11: Secretion of cytokines IL-8 and IL-1β by DCs, which were electroporated with components of the NFκB signaling pathway. DCs were produced from monocytes during a six-day culture with GM-CSF and IL-4. On Day 6, the DCs matured for 24 h after addition of a standard maturation cocktail (IL-1β, IL-6, TNFα and PGE2) (mDC). Then, the DCs were electroporated without RNA with IKKα-EE-A16-RNA (activates alternative signaling pathway), IKKβ-EEA10-RNA (activates classical signaling pathway) alone or in combination (15 μg of RNA each). 24 h after EP, the supernatants were collected and analyzed by an "inflammation cytometric bead array." The data from 3 independent donors are shown.

Figure 12:
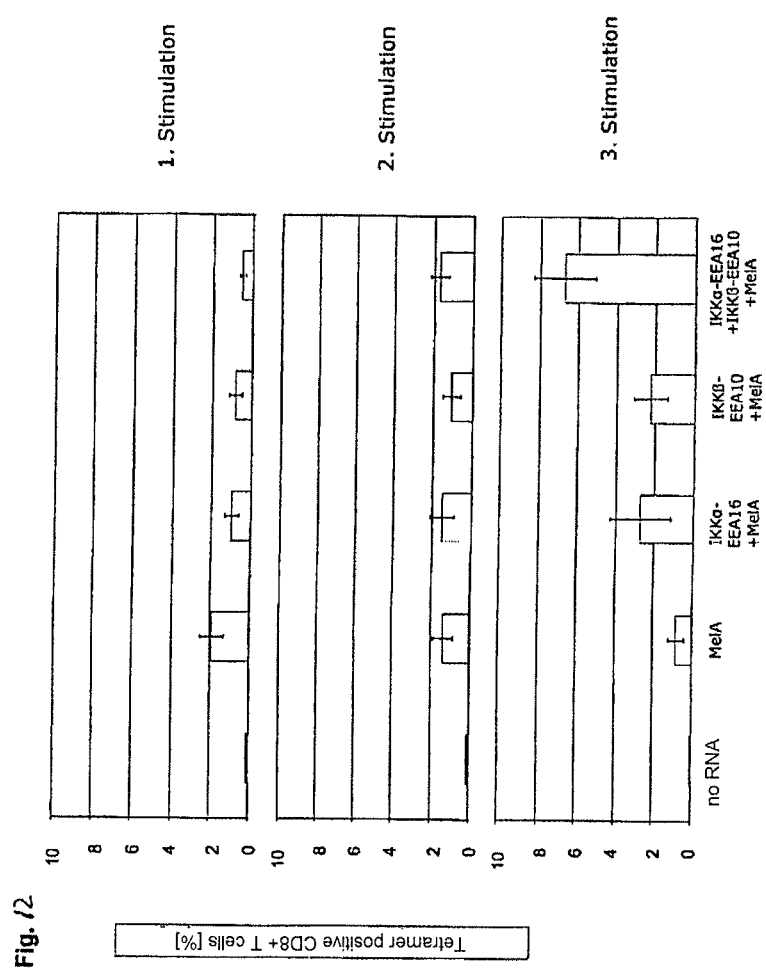

FIG. 12: Tetramer staining of the stimulation of autologous T cells with DCs, which were electroporated with RNA of components of the NFκB signaling pathway. Mature dendritic cells were electroporated without RNA, with IKKα-EE-A16-RNA (activates alternative signaling pathway), IKKβ-EEA10-RNA-(activates classical signaling pathway) alone or in combination (15 μg of RNA each). A portion of the DCs was coelectroporated with RNA encoding MelanA (MelA). 4 h after electroporation, autologous CD8$^+$ T cells were stimulated with these DCs in the ratio of 10:1. One week after the stimulation, the number of antigen-specific T cells was analyzed by tetramer staining, and the phenotype was identified by CCR7 and CD45RA staining. T cells were analyzed after an activating (1$^{st}$ stimulation) and two re-stimulations (2$^{nd}$ and 3$^{rd}$ stimulation). The mean of 5 independent donors is provided with the standard error of the mean.

Figure 13:
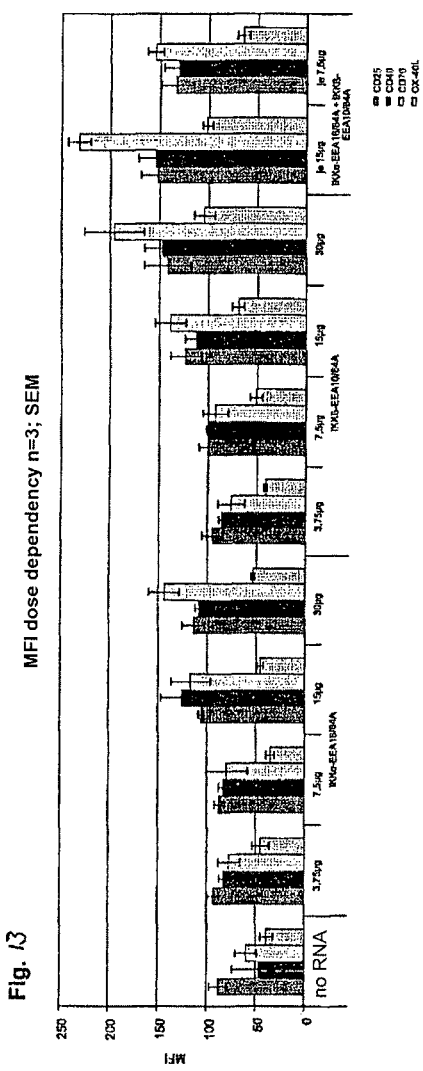

FIG. 13: Surface markers on DCs, which were electroporated with components of the NFκB signaling pathway with increasing concentrations of the transfected RNA. DCs were produced from monocytes during a six-day culture with GM-CSF and IL-4. On Day 6, the DCs matured for 24 h after addition of a standard maturation cocktail (IL-1β, IL-6, TNFα and PGE2) (mDC). Then, the DCs were electroporated without RNA, with IKKα-EE-A16-RNA (activates alternative signaling pathway), IKKβ-EEA10-RNA (activates classical signaling pathway) alone or in combination with increasing concentrations. These DCs were stained 24 h after EP with antibodies against CD25, CD 40, CD70, OX-40L, and analyzed by FACS. The mean of three independent donors is provided with the standard error of the mean.

Figure 14:
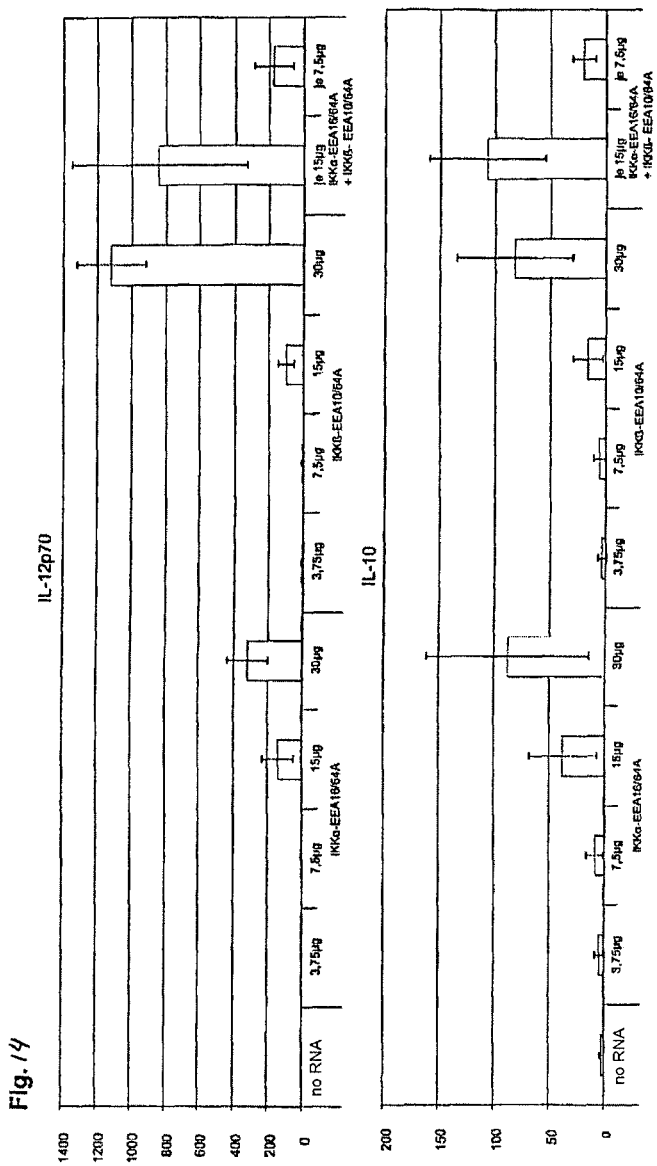

FIG. 14: Secretion of cytokines IL-12p70 and IL-10 by DCs, which were electroporated with components of the NFκB signaling pathway with increasing concentrations of the transfected RNA. DCs were produced from monocytes during a six-day culture with GM-CSF and IL-4. On Day 6, the DCs matured for 24 h after addition of a standard maturation cocktail (IL-1β, IL-6, TNFα and PGE2) (mDC). Then, the DCs were electroporated without RNA with IKKα-EE-A16-RNA (activates alternative signaling pathway), IKKβ-EEA10-RNA (activates classical signaling pathway) alone or in combination (with increasing concentrations). 24 h after EP, the supernatants were collected and analyzed by an "inflammation cytometric bead array." The mean of three independent donors is provided with the standard error of the mean.

Figure 15:
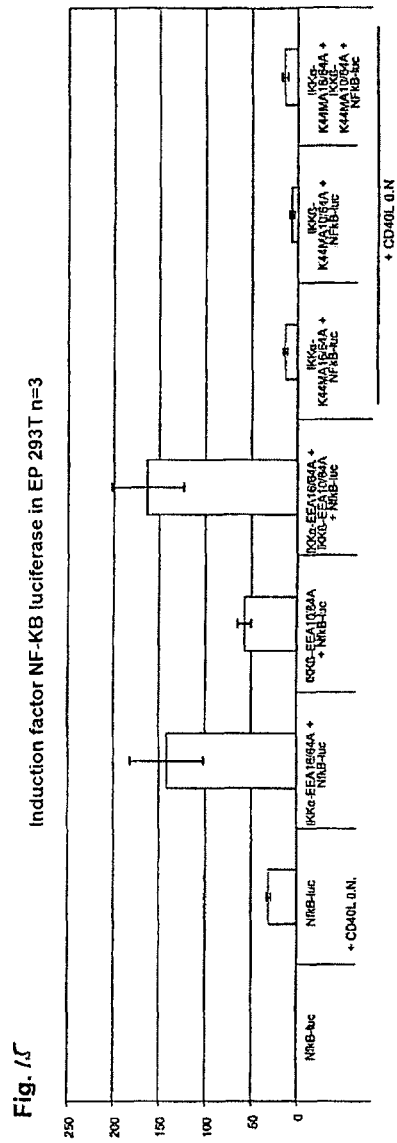

FIG. 15: Luciferase assay of 293T cells which were electroporated with components of NFκB signaling pathways. 293T cells were electroporated with activators (IKKα-EEA16-RNA or IKKβ-EFA10-RNA) or inhibitors of the NFκB signaling pathway (IKKα-K44M-A16-A10-RNA or IKKβ-K44M-A10-RNA) alone or in combination. All cells were coelectroporated with vectors encoding luciferase including an NFκB promoter. The NFκB signaling pathway of a portion of the cells was activated overnight with soluble CD40L. Luciferase activity was measured 24 hours after electroporation.

Figure 16:
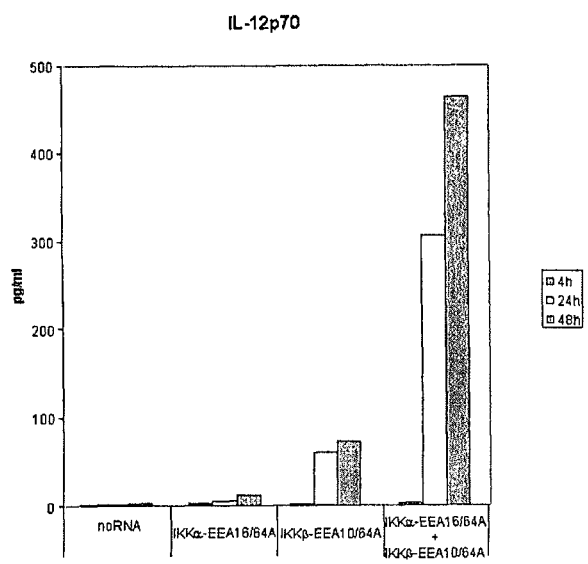

FIG. 16: Secretion of IL-12p70 by mature dendritic cells, which were transfected with RNA encoding constitutively active IKK mutants.

Figure 17:
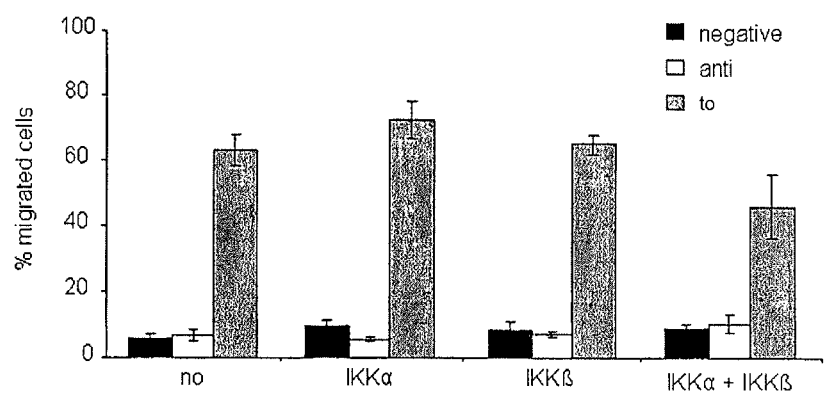

FIG. 17: Migration of mature dendritic cells which were transfected with RNA encoding constitutively active IKK mutants.

DETAILED DESCRIPTION OF THE INVENTION

The present invention relates to dendritic cells (DCs), the NFκB signaling pathway of which has been manipulated by RNA transfection with one or more nucleotide sequences encoding at least one mutant signal transducing protein of the NFκB signaling pathway. The invention further relates to dendritic cells, the NFκB signaling pathway of which has been manipulated by RNA transfection, to the manufacture thereof and to use thereof. It is based on the finding that DCs can be manipulated in their NFκB signaling pathway by RNA transfection and expression of mutant signal transducing proteins of the NFκB signaling pathway.

According to the invention, the term "dendritic cells" is used as in the prior art. In the immature state, they are characterized by low levels of MHC proteins and B7 co-stimulatory molecules, and the ability to phagocytosis and pinocytosis, and by the absence of the surface molecules CD83 and CD25. In the mature state, they are characterized by, inter alia, an altered pattern of cell surface proteins, wherein the surface expression of some or all of the following molecules is increased: CD25, CD40, CD70, CD80, CD83, CD86, and MHC proteins. "Mature" DCs are different from "immature" DCs, inter alia, in that the former are immunostimulatorily more active, usually retain the ability to migrate into the draining lymph nodes in vivo, and to present increasingly endogenously expressed and exogenous antigen in the MHC context. Under physiological conditions, only "mature" DCs are able to activate naive T cells.

According to the invention, the term "RNA transfection" is used as in the prior art. Accordingly, RNA transfection refers to introducing foreign RNA in a eukaryotic cell, a DC according to the invention, preferably a human DC. According to the invention, "nucleotide sequences" include DNA and RNA. Preferably, the RNA to be transfected is mRNA, which contains no introns. A definition of mRNA can be found in the prior art (see "Molekulare Genetik", Knippers, 9th revised edition, Thieme Verlag, 2006). The immunomodulatory efficiency of the DCs of the invention can be further increased by stabilizing the mRNA. This can take place, for example, by adding a cap analog during the in vitro transcription of the mRNA. The use of so-called ARCA ("anti-reverse cap analog") technology leads to a 100% correct orientation of the cap and therefore to a further increase in efficiency (Stepinski et al., RNA 7 (10), 2001, 1486-1495). Alternatively, the stability of the mRNA can be increased by attaching a cap structure enzymatically on the mRNA already synthesized in vitro, for example, as described in Tcherepanova et al., BMC Mol. Biol. (2008), 9:90. The stability of the mRNA can be further increased by attaching untranslated regions (UTR), such as of the β-globin mRNA (cf., e.g., Yu et al., Mol. Cell Biol. 21(17) (2001), 5879-5888).

An improvement in translation efficiency together with an expected improvement of the immunomodulatory properties of the DCs can also be achieved through the use of the capping methods described in the previous paragraph, as well as by known methods such as the insertion of an "internal ribosome entry site" (IRES) at the 5' end of the in vitro translated RNA (Tan et al., Hum. Immunol. 69(1), 2008, 32-40). The translated protein yield in transfection experiments can be increased generally and so also in the context of the present invention, by extending the length of the polyA tail. This technology leads to even better results if it is applied together with the ARCA technology (Mockey et al. Biochem. Biophys. Res. Commun. 340(4) (2006), 1062-1068).

In relation to the present invention, a "mutant signal transducing protein of the NFκB signaling pathway" is defined as a protein, which is a component of the known signal cascade that leads to activation of NFκB and the subsequent translocation of this protein into the cell nucleus. According to the invention, this term encompasses further proteins that interact in a modulatory manner with components of the signal cascade and influence its activity. Compared with corresponding wild-type proteins, all of these proteins have changes (mutations). The corresponding mutations are defined, inter alia, by deletions, extensions or, preferably, the substitution of one or more amino acids.

In relation to the present invention, the definition of the NFκB signaling pathway comprises the classical and the alternative signaling pathway. The classical signaling pathway is activated by microbiological and viral infections or by cytokines. In this context the IKK complex consisting of IKKα, IKKβ and NEMO induces the degradation of I—KB by phosphorylation, whereupon the transcription factor NFκB translocates into the cell nucleus and activates various target genes. The alternative NFκB signaling pathway is independent of IKK and NEMO. Here, IKKα interacts with p100 (NFκB2) that is processed into its p52 shape and together with RelB translocates into the cell nucleus and activates target genes.

"Manipulations" of the NFκB signaling pathway with respect to the present invention can be measured by a change in activity of dendritic cells. This includes changes in the secretion of IL12p70, the secretion of IL-10, the migration or the expression of various induction factors, such as OX-40L or CD25. Preferably encompassed is the (increased) secretion by dendritic cells transfected with constitutively active mutants of IKKα and/or IKKβ, of IL12p70 at preferably at least 5-fold, more preferably at least 10-fold, even more preferably at least 30-fold, and most preferably at least 50-fold increased levels compared with dendritic cells transfected with control RNA or non-transfected dendritic cells, which preferably are mature dendritic cells. Furthermore, preferred is the secretion of IL-10 at at least 5-fold, more preferably at least 10-fold and most preferably at least 30-fold increased levels by dendritic cells, preferably immature dendritic cells preferably transfected with constitutively active mutants of IKKα and/or IKKβ and are compared with untransfected or control RNA-transfected dendritic cells. Preferred may be also a high IL-12p70 secretion in conjunction with low IL-10 secretion at a ratio of IL-12p70 to IL-10 of preferably at least 3, more preferably at least 5, even more preferably at least 10 and most preferably at least 20, by preferably mature dendritic cells transfected with constitutively active mutants of IKKα and/or IKKβ.

Via RNA transfection of dendritic cells, the inventors were able to demonstrate in the present invention, surprisingly, that dendritic cells modified by RNA transfection can be manipulated in their function via the NFκB signaling pathway. The RNA transfection of various RNAs into dendritic cells can lead to either immunostimulation or tolerance induction or suppression of immunological responses. Transfected RNAs may enhance the secretion of IL-12p70, and thus lead to an immunostimulation. A further surprising effect of the present invention is based on the fact that identical RNAs, such as RNAs encoding constitutively activating mutants of IKKα and IKKβ, have different effects on the immunostimulation of dendritic cells, depending on the time of their RNA transfection (see FIGS. 2a and 2b).

According to the invention, immunostimulation is observed in transfection of mature DCs with RNAs, the transcription of which results in proteins in which the serine residues that are phosphorylated at physiological activation of IKK and thereby mediate the kinase activity of IKK, are replaced by glutamine residues. This allows, for example, in simultaneous presentation of tumor antigens by the DC, an effective killer T cell activation to be achieved, which can be exploited in the patients in combating tumors after administration of the transfected (autologous) DCs. This principle can be applied accordingly in other diseases. By contrast, if the RNA transfection is performed with immature DCs, according to the invention, an immunosuppressive effect is expected, since such DCs secrete large amounts of the immunosuppressive IL-10. Both alternatives represent preferred embodiments of the invention. Surprisingly, it was also shown that mature DCs of the invention are capable of migration (see FIG. 5). Such control of the immunological activity of dendritic cells is a major advance for medical use, for example in the form of vaccination with dendritic cells for the treatment of cancer patients.

According to the invention, said immunomodulatory, especially antigen-presenting, properties of the DCs can be further enhanced when, in addition to the RNA encoding said mutant signal-transducing protein(s), inhibitory RNAs such as siRNAs are introduced into the DCs or expressed there to inactivate mRNAs encoding immunosuppressive proteins such as, inter alia, A20, IL-10, TGF. Such a method is described in Breckpot et al. J. Immunol. 182(2) (2009), 860-870. A higher, more efficient induction of antigen-specific cytolytic activity by the DCs as an antigen presenting cell is also expected when immune-proteasome mRNA is inactivated therein, for example by siRNAs (Dannull et al., Blood 110(13) (2007), 4341-4350). An enhanced effect of DC-mRNA vaccines, for example in the fight against cancer, is also expected after stimulation of the DCs by single- or double-stranded RNA sequences (cf., e.g., Diebold et al., Science 303 (2004), 1529-1531).

Suitable preferred mutant signal-transducing proteins of the NFκB signaling pathway are mutants of the inhibitor of kappa kinases IKK, preferably constitutively active IKKα or IKKβ mutants, or IKKα or IKKβ inhibitory mutants. For the manufacture of the DCs according to aspect (1) of the invention several constitutively active or dominant-negative mutants of different IKKs have been manufactured experimentally. In this context, constitutively active IKKα and IKKβ mutants are preferably those which, starting from the corresponding wild-type sequences, preferably from SEQ ID NO:1 and 4, respectively, have one or more substitutions of Ser by Glu in the active site.

Preferred are such IKKα mutants in which one or more of the amino acid residues Ser176 and Ser180 of the IKKα wild-type of SEQ ID NO:1 is replaced by Glu, particularly preferably amino acid residues Ser176 and Ser180 of the IKKα wild-type of SEQ ID NO:1 are replaced by Glu, and optionally one or more of the destabilizing C-terminal serine and threonine residues, preferably destabilizing serine and threonine residues at positions 661, 662, 665, 669, 670, 676, 679, 680, 686, 687, 693, 695, 699, 705, 706, 721 and 722, and in a less preferred form 661, 662, 665, 669, 670, 676, 679, 680, 686, 687, 692, 694, 698, 704 and 705 of the wild-type of SEQ ID NO:1 are replaced by alanine residues. All mentioned IKK mutants, which are characterized by the insertion of alanine residues, lead to a stabilization of the protein and are furthermore characterized in that they enhance the effect of increased or inhibitory activity, respectively. In addition, in all embodiments of the invention, the introduction of the stabilizing alanine residues into the proteins represents preferred embodiments. Preferably, at least two, preferably at least three, more preferably at least four, more preferably at least eight, and particularly preferably all of said residues are replaced by alanine residues. According to the invention all possible permutations, even if they are not mentioned here, are explicitly included in the disclosure of this specification as if they were specified individually herein. Furthermore, those IKKβ mutants are preferred, in which one or more of the amino acid residues Ser177 and Ser181 of the IKKβ wild-type, preferably of SEQ ID NO:4, are replaced by Glu, particularly preferably the amino acid residues Ser177 and Ser181 of the IKKβ wild-type of SEQ ID NO:4 are replaced by Glu, and optionally one or more of the C-terminal destabilizing serine und threonine residues, preferably those destabilizing serine und threonine residues at positions 670, 672, 675, 679, 682, 689, 692, 695, 697 and 705 of the wild-type of SEQ ID NO:4 are replaced by alanine residues.

Particularly preferred are those constitutively active IKKα and IKKβ mutants comprising the amino acid residues 25 to 769 of SEQ ID NO:2 or the amino acid residues 18 to 773 of SEQ ID NO:5, preferably having the sequence of SEQ ID NO:2 or SEQ ID NO:5, or wherein the coding RNA sequence contains SEQ ID NO:3 or 6. Furthermore, each mRNA, which contains a sequence which may originate by silent mutations from sequence SEQ ID NO:3 or 6, as by, inter alia, codon optimization, is encompassed in the disclosure of this specification.

In this context, the inhibitory IKKα and IKKβ mutants are those which, starting from the corresponding wild-type sequences of SEQ ID NO:1 or 4, have a substitution of Lys by Met. Here, such IKKα mutants are preferred in which the amino acid residue Lys44 of the IKKα wild-type of SEQ ID NO:1 is substituted by Met, and optionally one or more of the destabilizing C-terminal serine und threonine residues, preferably destabilizing serine and threonine residues at positions 661, 662, 665, 669, 670, 676, 679, 680, 686, 687, 693, 695, 699, 705, 706, 721 and 722 of the wild-type of SEQ ID NO:1 are replaced by alanine residues. Further, such IKKβ mutants are preferred in which the amino acid residue Lys44 of the IKKβ wild-type of SEQ ID NO:4 is replaced by Met, and optionally one or more of the destabilizing C-terminal serine and threonine residues, preferably those destabilizing serine und threonine residues at positions 670, 672, 675, 679, 682, 689, 692, 695, 697 and 705 of the wild-type of SEQ ID NO:4 are replaced by alanine residues.

Particularly preferred are such inhibiting IKKα and IKKβ mutants comprising the amino acid residues 24 to 768 of SEQ ID NO:7 or the amino acid residues 24 to 779 of SEQ ID NO:9 and preferably having the sequence of SEQ ID NO:7 or SEQ ID NO:9, or having the RNA sequence of SEQ ID NO:8 or 10, or the RNA sequence of which can be converted by silent mutations in the RNA sequence of SEQ ID NO:8 or 10.

Another particularly preferred embodiment, as mentioned above, relates to dendritic cells of the invention, wherein the DCs (i) are mature DCs; and/or (ii) are NFκB-activated DCs producing IL-12p70; and/or (iii) are NFκB-activated DCs producing IL-10; and/or (iv) are also loaded with one or more target antigens.

In the present invention, the definition of "target antigen" includes peptide chains that are attached to the major histocompatibility complex (MHC), for example, and are presented on the cell surface of dendritic cells, T cells. They can be derived, inter alia, from a tumor antigen such as MelanA, GP100, members of the MAGE family, but also mutant tumor antigens such as BRAF-V600E and GNAQ-Q209L. But sources of non-defined antigens can also be used, such as tumor lysate or mRNA isolated from the tumor. Also, any viral protein may be an antigen source, such as HIV-1 NEF or influenza matrix protein.

The above-mentioned mutants may be expressed in DCs by RNA transfection of corresponding mRNA molecules. The RNA transfection is not a genetic change of the DCs, and is thus safe from a clinical point of view. Following the transfection of DCs with a constitutively active IKK mutant, after having been incubated with cytokines IL-1β, IL-6, TNFα and PGE2 ("matured"), they started to secrete the proinflammatory cytokine IL-12p70 (FIG. 2a), which is thought to play a crucial role in the induction of robust, long-lasting immune responses. Regarding the maturation of DCs, in addition to IL-1beta, IL-6, TNF and PGE2, alternatively or in addition, other substances may be used for maturation of DCs, including but not limited to: IFN-alpha, -beta, -gamma, artificial and natural TLR agonists, such as, inter alia, polyI:C, CpG, LPS, flagellin, or soluble and surface-bound substances that specifically bind surface receptors of the DCs.

Figure 1:
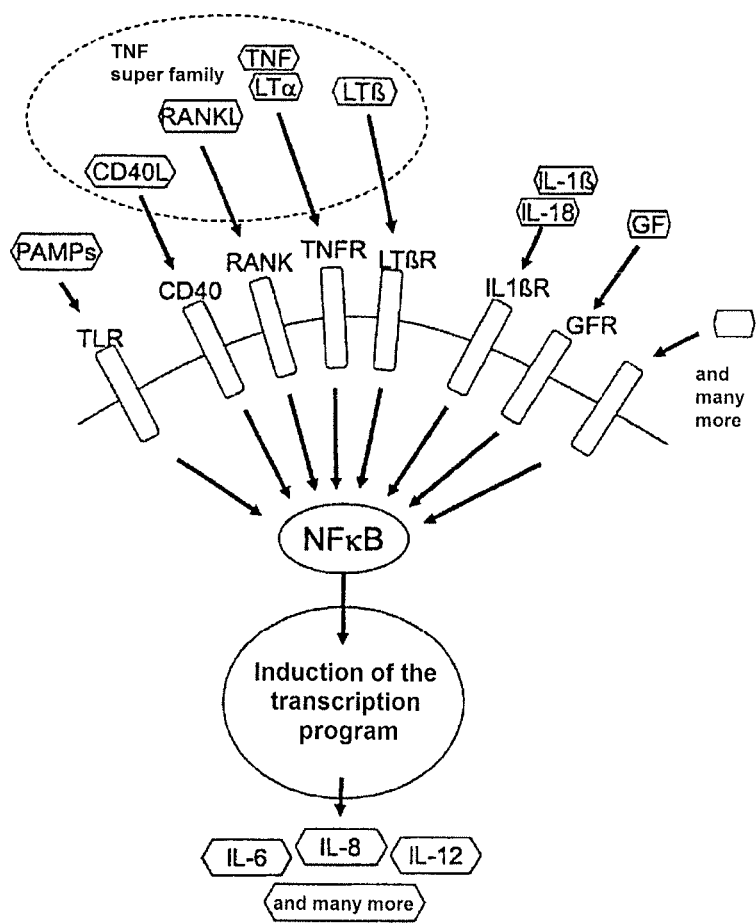
FIG. 1: NFκB is at the center of the DC maturation signal chain. A variety of surface receptors that are triggered by danger signals, and proinflammatory stimuli, which are known to trigger DC maturation, cause activation of NFκB. NFκB activation in turn causes the release of important cytokines such as IL-12p70 and phenotypic changes of the DCs.
Figure 2A:
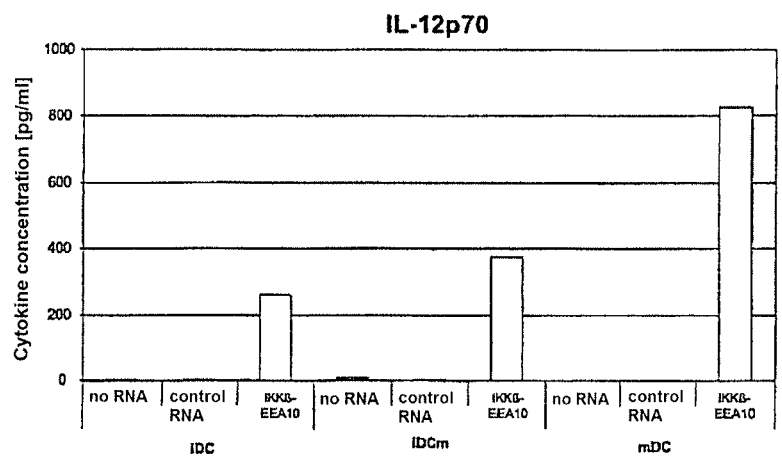
FIG. 2: Secretion of IL-12p70 (a) and IL-10 (b) by IKKβ-EEA10-RNA electroporated dendritic cells.
Figure 2B:
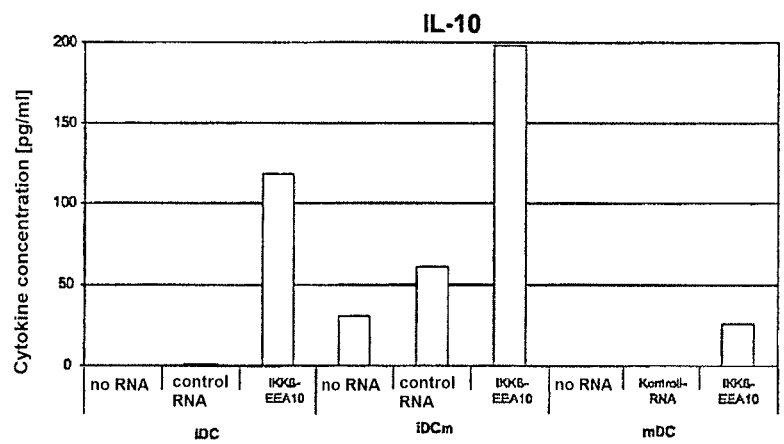
Figure 3:
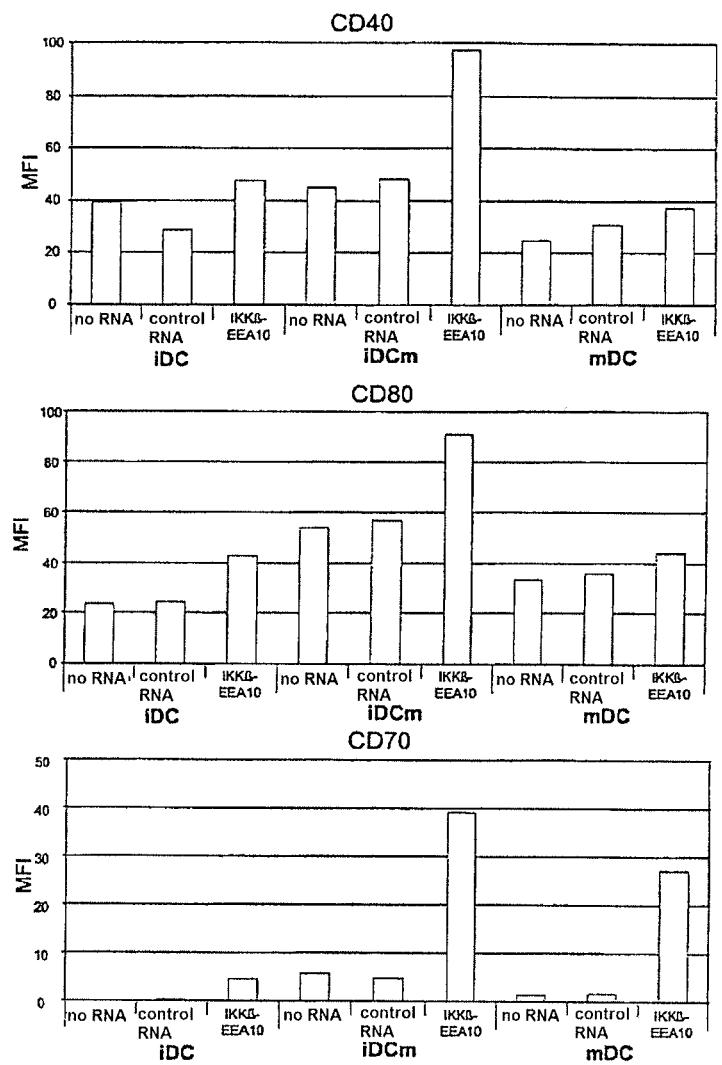
FIG. 3: Expression of surface markers on dendritic cells, transfected with the NFκB signaling component IKKβ-EEA10.
Figure 4A:
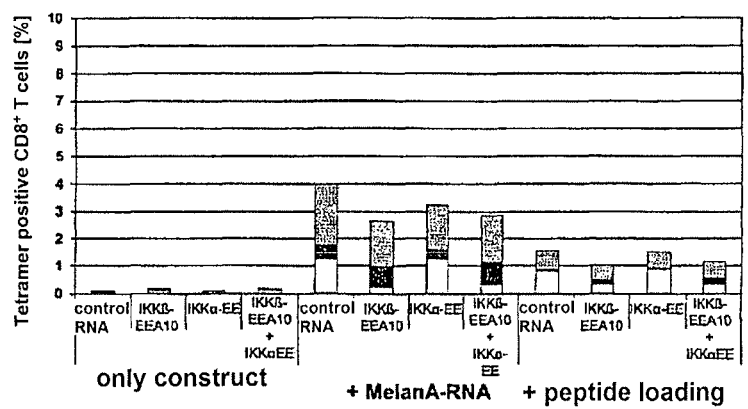
FIG. 4: Tetramer staining of the stimulation of autologous T cells with dendritic cells, electroporated with one or two RNAs encoding constitutively activated mutants of IKKα and IKKβ, and analyzed after a priming (a) and after a restimulation (b).
Figure 4B:
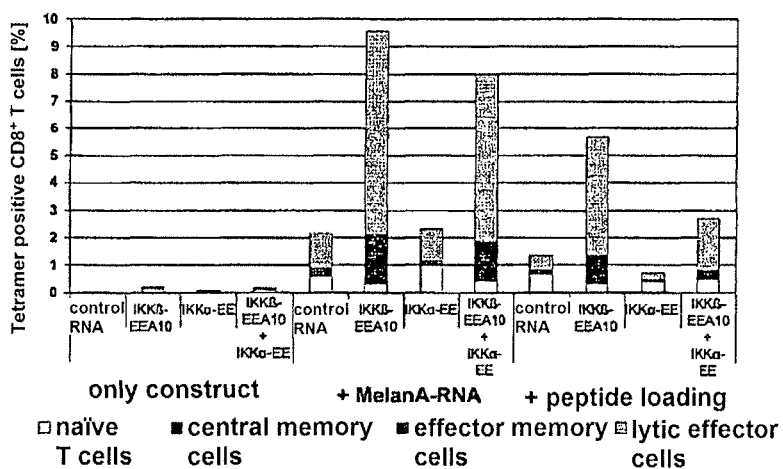
Figure 5:
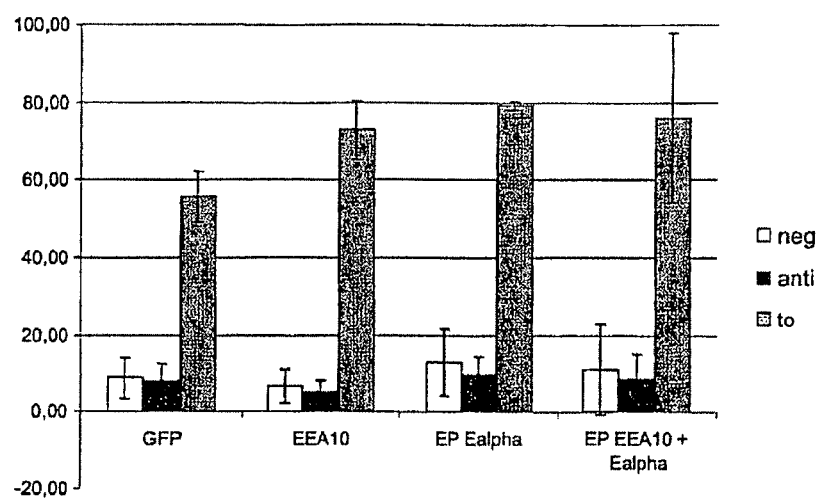
FIG. 5: Migration of mature dendritic cells 24 h after RNA transfection with one or two RNAs encoding constitutively activated mutants of IKKα and IKKβ.

However, if RNA transfection with the activating mutants took place at the beginning of maturation (ie., in immature DCs), DCs formed that released large amounts of cytokine IL-10, which is immunosuppressive under certain conditions (FIG. 2b). Furthermore, following RNA transfection of the RNAs described above, various maturation markers on the DCs showed increased expression, including those that are thought to play a role in the communication of the DCs with other cells of the immune system (FIG. 3). In this context, particularly, the surface molecule CD70 is of interest because it is thought to play a role in the induction of long-lived memory T cells (FIG. 3, bottom). The phenotype of long-lived memory T cells was described earlier. When DCs treated in this manner were used to stimulate autologous CD8+ T cells repeatedly, it was observed that NFκB activation enabled the DCs to further expand said T cells upon restimulation, wherein the T-cell phenotype of the effector memory cells was increasingly represented (FIG. 4). Another critical factor in the manufacture of immunogenic DCs is their ability to migrate, which is usually lost in IL-12-secreting DCs. Surprisingly, DCs transfected with the constitutively active NFκB mutants were able to migrate as efficiently towards the chemokine MIP-3β, as DCs, which were electroporated with a control RNA (FIG. 5). Thus, the RNA transfection of DCs with mRNA encoding functional mutants of the NFκB signaling pathway, is a new and innovative method for the generation of immunogenic or tolerogenic DCs whose actual clinical application is looming.

In further preferred embodiments of the invention, the DC is co-transfected with mRNAs encoding CD70, optionally in combination with those encoding caTLR4 and CD40 ligand or OX40L. All molecules mentioned in this application, which are introduced into the preferably human DCs encode, preferably, molecules, which correspond to those present in humans in respect to their amino acid sequence, or are derived from them.

According to aspect (2) of the invention, the method for the ex vivo manufacture of DCs, the NFκB signaling pathway of which has been manipulated, comprises the RNA transfection of immature or mature DCs with one or more nucleotide sequences encoding a mutant signal transducing protein of the NFκB signaling pathway described above. Here, preferably, RNA transfection takes place by electroporation (other methods known to the person skilled in the art, such as lipofection, etc. may also be used). A preferred embodiment of the electroporation process is the method described by Tuyaerts et al. which is particularly well suited for clinical applications (Cancer Gene Ther. 10(9) (2003), 696-706, the contents of which is expressly incorporated herein by reference). In a further preferred embodiment, the RNA transfection technology used is nucleofection (proprietary technology of Amaxa) (cf., e.g. Melhem et al., Clin. Vaccine Immunol. 15(9) (2008), 1337-1344). Preferred concentrations for transfection of RNA by electroporation include, in particular, about 1 µg/100 µl to about 100 µg/100 µl, more preferably 2 µg/100 µl to 50 µg/100 µl, and most preferably about 20 µg to about 40 µg/100. Besides the already mentioned electroporation, which may be effected both by a square wave pulse, as well as by an exponentially decaying pulse, mRNA transfection can be achieved by various reagents for mRNA transfection. Examples include charged and uncharged lipids by means of which DCs may be transfected with mRNA.

In the case of RNA transfection of immature DCs, the process of the invention may include further treating with a maturation stimulus. Other preferred embodiments include loading the DCs with a target antigen and/or (iii) the cryopreservation of mature DCs.

Herein, "maturation stimulus" is defined as molecules and combinations of molecules under the assistance of which immature dendritic cells become mature dendritic cells. A preferred combination of molecules herein consists of IL-1β, IL-6, TNFα and PGE2.

In relation to the present invention, "cryopreservation" is understood to be the storage of cells by freezing at temperatures below −75° C.

The composition, pharmaceutical composition or drug according to the aspect (3) of the invention may optionally include pharmaceutically acceptable excipients and carrier compounds. For pharmaceutical use, preferably, the DCs are autologous DCs.

A "pharmaceutical composition" or "drug" includes the dendritic cells of the invention and one or more components that are administered to patients, for example, in the form of a vaccination for the treatment of cancer or HIV. Processes and means of formulating a pharmaceutical composition are known to the person skilled in the art and may be found, for example, in Ansel et al., "Pharmaceutical Dosage Forms and Drug Delivery Systems", 7th edition, Lippincott Williams & Wilkins Publishers, 1999. The pharmaceutical composition or drug may be administered to an individual in an appropriate dose. In particular, the administration can be parenteral, for example, intravenous, intraperitoneal, subcutaneous or intramuscular, or via a catheter at a site in an artery. Preparations for parenteral administration include sterile aqueous or non-aqueous solutions, suspensions and emulsions. Examples of non-aqueous solvents are propylene glycol, polyethylene glycol, vegetable oils such as olive oil, and organic ester compounds such as ethyl oleate, which are suitable for injections. Aqueous carriers include water, alcoholic-aqueous solutions, emulsions, suspensions, salt solutions and buffered media. Parenteral carriers include sodium chloride solutions, Ringer's dextrose, dextrose and sodium chloride, lactated Ringer's solution and bound oils. Intravenous carriers include, for example, liquid, nutritional and electrolyte supplements (such as those that are based on Ringer's dextrose). The pharmaceutical composition or drug may also include preservatives and other additives, such as, for example antimicrobial compounds, antioxidants or complexing agents. Furthermore, depending on the specific use intended, other agents such as interleukins, growth factors, differentiation factors, interferons, chemotactic proteins, or a non-specific immunomodulating agent may be included.

The type of dosage is determined by the treating physician according to clinical factors. The person skilled in the art knows that the type of dosage depends on various factors, such as body size or weight, body surface area, age, sex or general health of the patient, but also on the particular agent to be administered, the duration and route of administration, and other drugs that may be administered in parallel. A typical dose can be, for example, in a range between 5 million and 50 million DCs per administration.

The schedule of repeated administration usually starts out with smaller intervals in the range of one to two weeks, and later on, intervals can be extended up to 6 months. In previous studies, DCs were usually injected intradermally, subcutaneously and intravenously.

"Suitable excipients and carrier compounds" include components onto which the cells of the invention may be applied or introduced and, for example, protect the cells. Examples of suitable pharmaceutically acceptable excipients and carrier compounds are known to the person skilled in the art and include, for example, phosphate buffered saline, water, emulsions, such as oil/water emulsions, various types of wetting agents or detergents, sterile solutions, etc. Pharmaceutical composition or drugs comprising such carriers can be formulated by means of known conventional methods.

"Autologous" dendritic cells are understood to mean the body's own cells of a patient or cells formed from the body's own cells of a patient.

In the use of the DCs of the invention for the stimulation of autologous $CD8^+$ T cells ex vivo according to the aspect (4) of the invention, preferably, (i) NFκB-activated DCs are used for passive T cell transfer and generation of a T cell clone (including subsequent TCR isolation), and (ii) NFκB-repressed DCs are used for expansion of Tregs for the treatment of allergies, chronic inflammation, autoimmunity and transplant rejection.

"$CD8^+$ T cells" are characterized by the presence of the surface marker CD8 and are members of a subset of T lymphocytes, which are able to kill infected somatic cells or tumor cells.

Passive immunization or "passive T cell transfer" is understood to mean the transfer of immunological effectors or T cells generated outside of the recipient. Recipients do not have to actively develop the immune response themselves, but receive it from the outside, thus they themselves are passive. Passive immunization with T cells, which is the passive transfer of T cells, is also referred to as an adaptive T cell transfer.

In relation to the present invention, a "T cell clone" is a population of cells derived from a T cell of a patient and which may be held in culture, originating from an individual T cell.

"Expansion of Treg" refers to the cultivation and proliferation of regulatory T cells, which can suppress the functions of other T cells.

"Allergies" refers to an overshooting immune response of the immune system to specific and normally harmless environmental substances (allergens).

"Autoimmunity" may be defined as an overshooting immune response of the immune system to the body's own tissues.

"TCR isolation" refers to a method for obtaining the nucleotide sequences encoding the T cell receptor (TCR) from a T cell clone. Methods for this purpose can be found in the prior art.

In the use of the DCs of the invention for the manufacture of a drug for the treatment of diseases in a patient according to aspect (5) of the invention and in the method for the treatment of cancer, infectious or autoimmune diseases in a patient, comprising administering the DCs of the invention to said patient according to aspect (7) of the invention, preferably NFκB-activated DCs are used for the DC-based vaccination (especially in the absence of helper epitopes or functional helper cells, and when the use of potent adjuvants is not possible), for therapeutic vaccination against cancer or infectious diseases (including HIV) and as a preventive vaccine, and NFκB-repressed DCs are used for the induction of tolerance in vivo, and for the treatment of allergies, chronic inflammation, autoimmunity and transplant rejection.

"DC-based vaccination" describes a method for administration of dendritic cells to patients, preferably by injection.

"Helper epitopes" are presented in the MHC/HLA Class II-context and can induce T-cell proliferation and the synthesis of cytokines.

"Functional helper cells" are a group of T-lymphocytes in the blood, which have a helper function. They are classified in two major subgroups based on the cytokines they release. One sub-group is involved in the cellular immune response, while the other sub-group is involved in the humoral immune response.

"Adjuvants" are excipients, which enhance the effect of a reagent or a pharmaceutical composition, in particular the immune response.

"Cancer" refers to a malignant tumor or a malignant leukemia.

"Infectious diseases" are caused by a pathogen, such as viruses, bacteria, fungi or other microorganisms.

In the present application, the "induction of tolerance in vivo" refers to the repression of an immunological response in patients, preferably in a human patient.

In the process for the expansion of T cells, including the stimulation of autologous CD8$^+$ T cells ex vivo, comprising stimulating the T cells with DCs of the invention according to aspect (6) of the invention, preferably NFκB activated DCs are used for T cell expansion of T cells for the passive T cell transfer and generation of a T cell clone (e.g., for subsequent TCR isolation), and NFκB-repressed DCs are used for expansion of Tregs for the treatment of allergies, chronic inflammation, autoimmunity and transplant rejection.

A desired improved T cell proliferation, and thus an improved medicinal effect may also be achieved by the co-administration or simultaneous expression in the DC via transfected mRNA(s) of antibodies, preferably against CTLA-4, PD-L1, PD-L2, PD1, or by an agonistic anti-GITR antibody (cf., e.g., Leach et al., Science 271 (1996), 1734-1736; Quezada et al., J. Clin. Invest., 116(7) (2006), 1935-1945).

A further embodiment relates to a method for the treatment of diseases in a patient, comprising administering the DCs of the invention to said patient, wherein preferably (i) NFκB-activated DCs are used for DC-based vaccination (especially in the absence of helper epitopes or functional helper cells, and when the use of potent adjuvants is not possible), for the therapeutic vaccination against cancer or infectious diseases (including HIV) and/or as a preventive vaccine, and (ii) NFκB-repressed DCs are used for the induction of tolerance in vivo, and for the treatment of allergies, chronic inflammation, autoimmunity and transplant rejection.

Potential therapeutic applications of dendritic cells will be discussed below. A possible strategy for the treatment of a cancer patient involves obtaining monocytes from the blood of said patient, the differentiation of these monocytes into dendritic cells (DCs) by means of GM-CSF and IL-4, or similarly acting cytokines; the maturation of said DCs by IL-1beta, IL-6, TNF, and PGE2, or similarly acting maturation stimulators; the electroporation of said DCs with mRNA the sequence of which encodes one or both of the NFkappaB-activating mutants of IKK-alpha and IKK-beta; the loading of said DCs with one or more tumor-associated antigen(s) by either co-electroporation of an mRNA, the sequence of which encodes for it(them), or by exogenous loading of said DCs with one or more synthetic peptide(s) which can bind to HLA molecules of said DCs; the cryopreservation of said DCs in suitable portions; quality control of said DCs by determination of IL-12p70 secretion; the intravenous or intra- or subdermal injection of said DCs into said patient in multiple staggered doses.

According to the invention, in the manufacture of the DCs the direct recovery of DCs from fresh or cryopreserved patient material is contemplated, including but not limited to blood or blood cells or other tissue of the patient, by magnetic or fluorescence activated cell sorting or the differentiation of the DCs from bone marrow stem cells, which were purified, for example, via the stem cell marker CD34. For the differentiation of the monocytes and the stem cells to DCs, besides GM-CSF and IL-4, other substances may be used including, but not limited to: Flt3 ligand, IL-15, IFN-alpha, TNF.

Inter alia, autologous and allogeneic tumor material, and mRNA derived thereof and amplified, and also enzymatically produced mRNA encoding tumor antigens or parts thereof, may be used as antigen sources for antigen loading. HLA-binding peptides derived from tumor antigens may be loaded directly on the HLA molecules of the DCs. Genetically engineered tumor proteins or recombinant proteins combining tumor antigens, or parts thereof, with receptor agonists, which mediate the entry into the DCs, may also be used. These methods of antigen loading may be applied in the immature and/or mature stage of the DCs.

A possible strategy for the manufacture of antigen-specific cytotoxic T cells for the autologous or allogeneic adaptive T cell therapy involves the manufacture of NFkappaB-activated DCs, as described in the example, the isolation of T cells from fresh or cryopreserved patient material, including but not limited to blood or blood cells or other tissue of the patient, furthermore the antigen-specific proliferation of these T cells by repeated incubation with said NFκB-activated DCs, which are loaded with the corresponding antigen, the cryopreservation of the T cells in appropriate portions, quality control of the T cells by determining their antigen-specific lytic activity and their ability to antigen-specific cytokine secretion, the intravenous, intratumoral, intraperitoneal, or other injection of the T cells into said patient in one or more staggered doses.

Unless otherwise defined, the terms used herein have the same meaning as in the prior art.

The invention is further illustrated by the following examples, they do not limit the scope of the application by any means.

Sequence Listing, free Text:

| SEQ ID NO: | Description |
|---|---|
| 1 | Wild-type IKKα protein |
| 2 | IKKα-EEA16/64A protein (AS 1-24 TAG) |
| 3 | IKKα-EEA16/64A nucleotide sequence |
| 4 | Wild-type IKKβ protein |
| 5 | IKKβ-EEA10/64 protein (AS 1-17 TAG) |
| 6 | IKKβ-EEA10/64 nucleotide sequence |
| 7 | IKKα-K44MA16/64A protein (AS 1-23 TAG) |
| 8 | IKKα-K44MA16/64A nucleotide sequence |
| 9 | IKKβ-K44MA10/64 protein (AS 1-23 TAG) |
| 10 | IKKβ-K44MA10/64 nucleotide sequence |

EXAMPLES

Materials and Methods
Electroporation of DCs:

Mature or immature DCs were adjusted at about 40-60× $10^6$ cells/ml using OptiMEM (minimum volume for a 4 mm electroporation cell: 100 µl) and pipetted into the prepared cells. In the meantime, the cell was charged with RNA encoding IKKβ-EEA10, IKKα-EEA16. Electroporation was performed with the program square-wave pulse at 500 V for 1 ms (4 mm cell). Immediately after electroporation, the DCs were transferred into previously prepared DC medium (incl. IL-4 and GM-CSF) and incubated in an incubator for the following experiments. When immaturely transfected DCs were matured after electroporation, maturing cocktail (IL1-β, IL-6, TNFα and $PGE_2$) was added to the DC medium.

A: Sequences of Constitutively Active IKKα and IKKβ Mutants

1. IKKα-EEA16/64A Sequence (SEQ ID NO:2):

Comparison IKKα-EEA16/64A amino acid sequence (SEQ ID NO:2) with amino acid sequence of wild-type IKKα (SEQ ID NO:1): EE mutations (at pos. 200 und 204 of SEQ ID NO:2) cause constitutive activity of IKKα, A16 mutations (at pos. 685, 686, 689, 693, 694, 700, 703, 704, 710, 711, 717, 719, 723, 729, 730, 745 und 746 of SEQ ID NO: 2) remove destabilizing serines und threonines, leading to a largely increased stability of the protein. The corresponding nucleotide sequence is shown in SEQ ID NO:3.

2. IKKβ-EEA10/64 Sequence (SEQ ID NO:5):

Comparison IKKβ-EEA16/64A amino acid sequence (SEQ ID NO:5) with amino acid sequence of wild-type IKKβ (SEQ ID NO:4): EE mutations (at pos. 231 und 235 of SEQ ID NO:5) cause constitutive activity of IKKβ, A10 mutations (at pos. 724, 726, 729, 733, 736, 743, 746, 749, 751, und 759 of SEQ ID NO:2) remove destabilizing serines, leading to a largely increased stability of the protein. The corresponding nucleotide sequence is shown in SEQ ID NO:6.

B: Sequences of Inhibitory IKKα and IKKβ Mutants

3. IKKα-K44MA16/64A Sequence (SEQ ID NO:7):

Comparison IKKα-K44MA16/64A amino acid sequence (SEQ ID NO:7) with wild-type IKKα amino acid sequence. (SEQ ID NO:1). The kinase activity is inhibited by an exchange of the aa lysine (Lys44; pos. 67 in SEQ ID NO:7) at the ATP binding site by methionine. By dimerization, this mutant has a dominant negative effect. A16 mutations (pos. 684, 685, 688, 692, 693, 699, 702, 703, 709, 710, 716, 718, 722, 728, 729, 744, and 745 of SEQ ID NO:7) remove destabilizing serines and threonines, resulting in a largely increased stability of the protein. The corresponding nucleotide sequence is shown in SEQ ID NO:8.

4. IKKβ-K44MA16/64A Sequence (SEQ ID NO:9):

Comparison IKKβ-K44MA16/64A amino acid sequence (SEQ ID NO:9) with wild-type IKKβ amino acid sequence. (SEQ ID NO:4). The kinase activity is inhibited by an exchange of the aa lysine (Lys44; pos. 67 in SEQ ID NO:9) at the ATP binding site by methionine. By dimerization, this mutant has a dominant negative effect. A10 mutations (pos. 693, 695, 698, 702, 705, 712, 715, 718, 720, and 728 of SEQ ID NO:9) remove destabilizing serines, resulting in a largely increased stability of the protein. The corresponding nucleotide sequence is shown in SEQ ID NO:10.

Example 1: Secretion of IL-12p70 and IL-10 by IKKβ-EEA10-RNA-Electroporated Dendritic Cells Dendritic cells, immature (iDC) or mature (mDC) without RNA, were electroporated with a control RNA or IKKβ-EEA10-RNA (SEQ ID NO:6). Immediately after electroporation, half of the immaturely electroporated cells were matured (iDCm). Twenty-four hours after electroporation, the cytokine concentrations (IL-12p70 and IL-10) in the supernatants were determined in a cytometric bead array (CBA). FIGS. 2(a) and (b), respectively, show data of one representative of four independent experiments.

Example 2: Expression of Surface Markers on Dendritic Cells Transfected with the NFκB Signaling Pathway Component IKKβ-EEA10

Immature (iDC) and mature (mDC) dendritic cells were electroporated with RNA encoding IKKβ-EEA10 (SEQ ID NO:6). After electroporation, half of the immaturely electroporated cells were treated with maturation cocktail (iDCm). As control conditions, DCs were electroporated without RNA or with irrelevant RNA (control RNA). After electroporation, the DCs were cultured in DC medium for 24 h, harvested and stained with a PE-labeled antibody against CD40, CD80 and CD70. The PE label identifies the coupling of the pigment phycoerythrin and an antibody. The mean fluorescence intensity (MFI) of the electroporated dendritic cells was determined by flow cytometry. The values given in FIG. 3 show the specific MFI, which was calculated from the measured relative fluorescence minus the measured fluorescence of the isotype antibody. The data represent one representative of four independent experiments.

Example 3: Tetramer Staining of the Stimulation of Autologous T Cells with Dendritic Cells Electroporated with RNA of NFκB Signaling Pathway Components Mature dendritic cells were electroporated with control RNA, IKKβ-EEA10-RNA (SEQ ID NO:6) and IKKα-EE-RNA, or with a combination of IKKβ-EEA10 and IKKα-EE-RNA. A portion of the cells was co-electroporated with RNA encoding the tumor marker MelanA, (+ MelanA RNA). Three hours after electroporation, one half of the condition series without MelanA was loaded with MelanA/A2-peptide for 1 h (+ peptide loading). Four hours after electroporation, autologous CD8$^+$ T cells were stimulated with said dendritic cells in the ratio 10:1. After one week, the number of antigen-specific T cells was analyzed and their phenotype determined by CCR7 and CD45RA staining. Said T cells were analyzed following a priming FIG. 4(a) and after a restimulation FIG. 4(b).

The figures show data from one donor.

Example 4: Migration of Mature Dendritic Cells 24 h after RNA Transfection with NFκB Signaling Pathway Components Mature DCs were electroporated with RNA encoding GFP, IKKβ-EEA10 (SEQ ID NO:6) and IKKα-EE, alone and in combination. After electroporation, said DCs were cultured for 24 h and then tested for their ability to migrate for 2 h in a transwell assay. The results are shown in FIG. 5 (condition without chemokine (=neg); chemokine in the insert (=anti); chemokine in the depression (=to)). The data shown represent mean values with the standard deviation of three independent experiments.

Example 5: Improvement of DCs by RNA Transfection with NFκB Mutants

Stimulation of DCs with components of the NFκB signaling pathway, IKKβ-EE-A10 and IKKα-EE-A16 (SEQ ID NO:3): the following constructs were used: IKKβ-EE-A10 stimulates the classical NFκB signaling pathway leading to the activation and maturation of the DCs, and IKKα-EE-A16 is an activator of the alternative NFκB signaling pathway.

The effects of electroporation with IKKβ-EE-A10 were mainly an up-regulation of surface markers (CD25, CD40, CD70, CD80, CD83 and OX-40L, FIGS. 6-8) and an up-regulation of the cytokine secretion, and in particular of IL12p70, while IL-10 was secreted in very small amounts (FIG. 9). Other secreted cytokines were: IL-6, TNFα (FIG. 12), IL-8 and IL-1β (FIG. 11). These effects were enhanced as RNA of the activators of the classical and the alternative NFκB signaling pathway (IKKβ-EE-A10 and IKKα-EE-A16) were co-electroporated (FIGS. 6-11). Electroporation of IKKα-EE-A16 RNA alone had comparable effects as slightly smaller amounts of the secreted cytokines and the expression of surface markers (FIG. 6-11). Particularly after the third stimulation, electroporated mDCs showed a much greater stimulatory capacity in regards to autologous T cells (FIG. 12). DCs that were electroporated with only a single activator (IKKα-EE-A16 or IKKβ-EE-A10) had similar stimulatory capacities (up to three times compared to the control condition Mela), while the DCs, which were electroporated with both activators had the highest capacity for stimulation of specific T cells (seven-fold expansion of specific T cells).

Dose dependence experiments were performed to determine the best amount of RNA that should be used during the RNA transfection of DCs. Mature DCs were electroporated with increasing RNA concentrations. Increasing expression patterns of surface markers (CD25, CD40, CD70 and OX-40L) were obtained depending on the concentration of the transfected RNA (FIG. 13). But, nevertheless, the state of electroporation with both activators IKKβ-EE-A10 and IKKα-EE-A16 (15 μg each) led to an increased expression of all markers, in particular CD70, as compared to 30 μg of RNA from one activator alone.

In cytokine secretion, a dose-dependent up-regulation was obtained, in particular of IL12p70, whereas IL-10 was secreted in a very low amount (FIG. 14). Moreover, the secretion of IL-6, IL-8 and TNF was dose-dependent with a similar pattern (data not shown). Here, the amount of secreted cytokines was not higher when RNA of activators of the classical and the alternative NFκB signaling pathway (IKKβ-EE-A10 and IKKα-EE-A16) were co-electroporated (compare 30 μg of each RNA with a combination of 15 μg of RNA of both activators).

Example 6: NFκB Activity in Transfected 293T Cells 293T cells were electroporated with activators of both NFκB signaling pathways and co-electroporated with a vector encoding luciferase under the control of an NFκB promoter. In all cases (IKKα-EE-A16 and IKKβ-EE-A10 alone or in combination), luciferase activity was measured 24 h after electroporation (FIG. 15). Again, the case of RNA transfection with both activators showed the biggest effect.

This assay was also performed with DCs, but produced no results (data not shown).

IKKβ-K44M-A10 and IKKα-K44M-A16: Using an inhibitor of the classical (IKKβ-K44M-A10) and the alternative NFκB signaling pathway (IKKα-K44M-A16), a luciferase assay was performed with 293T cells which were electroporated with IKKα-K44M-A16 or IKKβ-K44M-A10 RNA alone or in combination, and were co-electroporated with luciferase vectors comprising an NFκB promoter. NFκB signaling pathways of transfected 293T cells were activated overnight with soluble CD40L. Luciferase activity was measured 24 h after electroporation. Both inhibitors were clearly able to reduce luciferase activity in comparison with the positive control, which has been transfected only with luciferase vector and activated with soluble CD40L (FIG. 15).

Example 7: Secretion of IL-12p70 in Mature Dendritic Cells that have been Transfected with RNA Encoding Constitutively Active IKK Mutants On Day 6, dendritic cells derived from monocytes were matured for 24 h using the standard maturation cocktail (IL-1β, IL-6, TNFα and PGE2) and then electroporated. Said cells were transfected without RNA, with RNA encoding the constitutively active mutants IKKαEEA16 and IKKβEEA10, and with a combination of both RNAs (see FIG. 16). Subsequently, the concentration of IL-12p70 in the medium was measured 4 h, 24 h and 48 h after electroporation. Here, the production of IL12p70 was observed over a period of 2 days. The use of both mutants led to the highest IL-12p70 production. One representative experiment of three is shown.

Example 8: Migration of Mature Dendritic Cells that have been Transfected with RNA Encoding Constitutively Active IKK Mutants On Day 6, dendritic cells derived from monocytes were matured for 24 h using the standard maturation cocktail (IL-1β, IL-6, TNFα and PGE2) and then electroporated. Said cells were transfected with 5 μg/100 μl of RNA encoding Melan A, and, with 15 μg/100 μl of RNA, encoding constitutively active mutants of IKKα and IKKβ, and encoding a combination of both RNAs (see FIG. 17). Then, the ability of the transfected cells to migrate to the chemokine CCL19 was studied. The results are shown in FIG. 17 (condition without chemokine (=neg); chemokine in the insert (=anti); chemokine in the depression (=zu)). Means with standard errors from 4 independent experiments are shown.

The invention claimed is:

1. Dendritic cells, the NFκB signaling pathway of which has been manipulated by RNA transfection with one or more nucleotide sequences encoding at least one mutant signal transducing protein of the NFκB signaling pathway, wherein the mutant signal transducing protein of the NFκB signaling pathway is a constitutively active IKKα or IKKβ mutant, wherein (i) the constitutively active IKKα mutant comprises the amino acid residues 25 to 769 of SEQ ID NO:2; or (ii) the constitutively active IKKβ mutant comprises the amino acid residues of SEQ ID NO:5.

2. The dendritic cells according to claim 1, wherein the constitutively active IKKα and IKKβ mutants have the sequence of SEQ ID NO:2 and SEQ ID NO:5, respectively, or have the RNA sequence of SEQ ID NO:3 or 6.

3. The dendritic cells according to claim 2, wherein said dendritic cells (i) are mature dendritic cells; and/or;

(ii) are NFκB-activated dendritic cells that produce IL-12p70; and/or (iii) are NFκB-activated dendritic cells that produce IL-10; and/or (iv) are further loaded with one or more target antigens.

4. A composition, pharmaceutical composition or drug comprising dendritic cells according to claim 2, and optionally pharmaceutically acceptable excipients and carrier compounds.

5. The composition, pharmaceutical composition or drug according to claim 4, wherein said dendritic cells are autologous dendritic cells.

6. The dendritic cells according to claim 1, wherein said dendritic cells
   (i) are mature dendritic cells; and/or;
   (ii) are NFκB-activated dendritic cells that produce IL-12p70; and/or
   (iii) are NFκB-activated dendritic cells that produce IL-10; and/or
   (iv) are further loaded with one or more target antigens.

7. A composition, pharmaceutical composition or drug comprising dendritic cells according to claim 6, and optionally pharmaceutically acceptable excipients and carrier compounds.

8. The composition, pharmaceutical composition or drug according to claim 7, wherein said dendritic cells are autologous dendritic cells.

9. A composition, pharmaceutical composition or drug comprising dendritic cells according to claim 1, and optionally pharmaceutically acceptable excipients and carrier compounds.

10. The composition, pharmaceutical composition or drug according to claim 9, wherein said dendritic cells are autologous dendritic cells.

11. Dendritic cells, the NFκB signaling pathway of which has been manipulated by RNA transfection with one or more nucleotide sequences encoding at least one mutant signal transducing protein of the NFκB signaling pathway, wherein the mutant signal transducing protein of the NFκB signaling pathway is a constitutively active IKKα or IKKβ mutant, wherein the constitutively active IKKα and IKKβ mutants have the sequence of SEQ ID NO:2 and SEQ ID NO:5, respectively, or have the RNA sequence of SEQ ID NO:3 or 6.

12. The dendritic cells according to claim 11, wherein said dendritic cells
   (i) are mature dendritic cells; and/or;
   (ii) are NFκB-activated dendritic cells that produce IL-12p70; and/or
   (iii) are NFκB-activated dendritic cells that produce IL-10; and/or
   (iv) are further loaded with one or more target antigens.

13. A composition, pharmaceutical composition or drug comprising dendritic cells according to claim 11, and optionally pharmaceutically acceptable excipients and carrier compounds.

14. The composition, pharmaceutical composition or drug according to claim 13, wherein said dendritic cells are autologous dendritic cells.

15. A composition, pharmaceutical composition or drug comprising dendritic cells according to claim 13, and optionally pharmaceutically acceptable excipients and carrier compounds.

16. The composition, pharmaceutical composition or drug according to claim 15, wherein said dendritic cells are autologous dendritic cells.

\* \* \* \* \*